United States Patent
Akirav

(10) Patent No.: US 10,858,706 B2
(45) Date of Patent: Dec. 8, 2020

(54) SYSTEM, METHOD AND KIT FOR ANALYSIS OF CIRCULATING DIFFERENTIALLY METHYLATED DNA AS A BIOMARKER OF BETA-CELL LOSS

(71) Applicant: NYU Winthrop Hospital, Mineola, NY (US)

(72) Inventor: Eitan Moshe Akirav, Plainview, NY (US)

(73) Assignee: NYU Winthrop Hospital, Mineola, NY (US)

( * ) Notice: Subject to any disclaimer, the term of this patent is extended or adjusted under 35 U.S.C. 154(b) by 17 days.

(21) Appl. No.: 15/743,402

(22) PCT Filed: Jul. 11, 2016

(86) PCT No.: PCT/US2016/041753
§ 371 (c)(1),
(2) Date: Jan. 10, 2018

(87) PCT Pub. No.: WO2017/011390
PCT Pub. Date: Jan. 19, 2017

(65) Prior Publication Data
US 2018/0208985 A1    Jul. 26, 2018

Related U.S. Application Data

(60) Provisional application No. 62/191,115, filed on Jul. 10, 2015.

(51) Int. Cl.
*C12Q 1/6883* (2018.01)
*C12Q 1/6858* (2018.01)

(52) U.S. Cl.
CPC ......... *C12Q 1/6883* (2013.01); *C12Q 1/6858* (2013.01); *C12Q 2600/154* (2013.01)

(58) Field of Classification Search
CPC ............... C12Q 1/6883; C12Q 1/6858; C12Q 2600/154
See application file for complete search history.

(56) References Cited

U.S. PATENT DOCUMENTS 9,127,317 B2  9/2015 Akirav
9,920,372 B2  3/2018 Akirav
10,221,457 B2 3/2019 Akirav

FOREIGN PATENT DOCUMENTS

WO   2013131083 A1   9/2013

OTHER PUBLICATIONS

Tan et al. Molecular Oncology. 2009. 3:425-438. (Year: 2009).*
Slieker et al. Epigenetics & Chromatin. 2013. 6, Article No. 26. (Year: 2013).*
Illunnina 450K Beadchip. Retrieved on Oct. 8, 2019 from the internet: https://support.illumina.com/array/array_kits/infinium-methylationepic-beadchip-kit/downloads.html. (Year: 2019).*
Kohler et al. EACR-23 Poster Sessions—No. 437. European Journal of Cancer. Jul. 2014. 50(Suppl. 5):S105. (Year: 2014).*
PCT International Search Report and Written Opinion, dated Dec. 15, 2016 in connection with PCT International Application No. PCT/US2016/041753, 10 pages.
Brethertion-Watt D, Insulin upstream factor 1 and a novel ubiquitous factor bind to the human islet amyloid polypeptide-amylin gene promoter, Biochem J., 1996, 313 (Pt 2): 495-502.
Olsen J.A. et al., Circulating Differentially Methylated Amylin DNA as a Biomarker of β-Cell Loss in Type 1 Diabetes, PLoS One., Apr. 25, 2016, 11(4):e0152662. doi:10.1371/journal.pone.0152662, pp. 1-15.

* cited by examiner

*Primary Examiner* — Joseph G. Dauner
(74) *Attorney, Agent, or Firm* — Amster, Rothstein & Ebenstein LLP

(57) ABSTRACT

β-cell loss in In Type 1 diabetes is typically undetected until the development of hyperglycemia, at which point β-cell mass is significantly reduced. Methylation sensitive quantitative real time PCR (qRTPCR) of demethylated circulating free β-cell specific DNA can be used as a biomarker of β-cell death. Such DNA includes insulin gene and amylin gene DNA. Detection may be by determination of a gene demethylation index. Methylated and demethylated DNA may be distinguished by bisulfite treatment and use of specific PCR primers or probes to detect the different bisulfite treatment products. Detection of demethylated circulating free amylin DNA is useful in identifying β-cell death. The amylin DNA may be used in conjunction with other β-cell specific genes, such as insulin, to provide a multi-gene approach towards the detection of β-cell loss.

15 Claims, 11 Drawing Sheets
Specification includes a Sequence Listing.

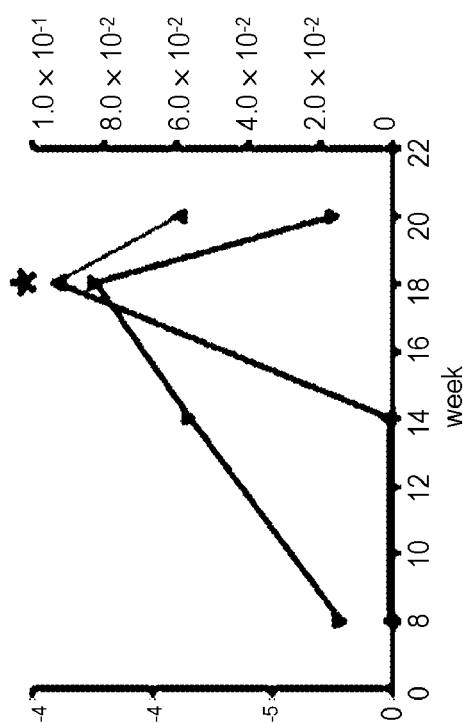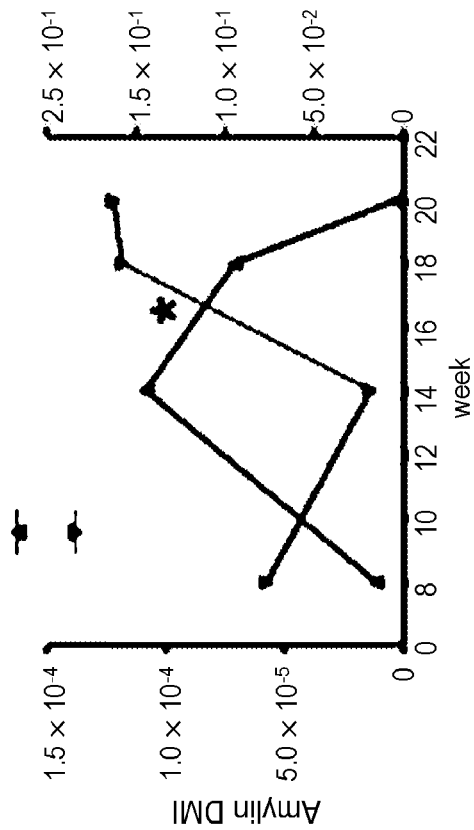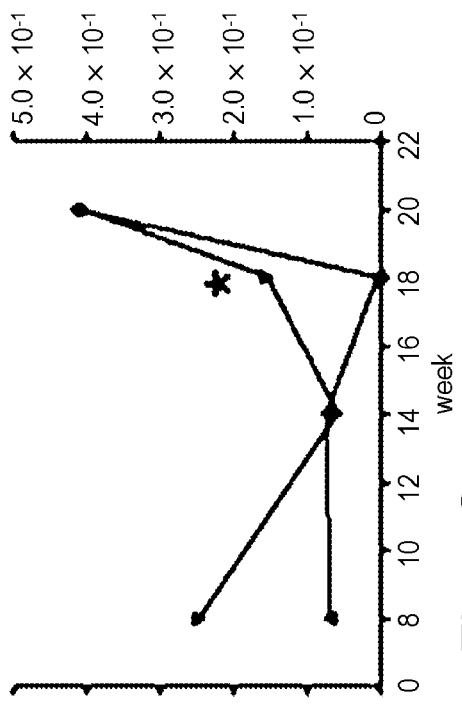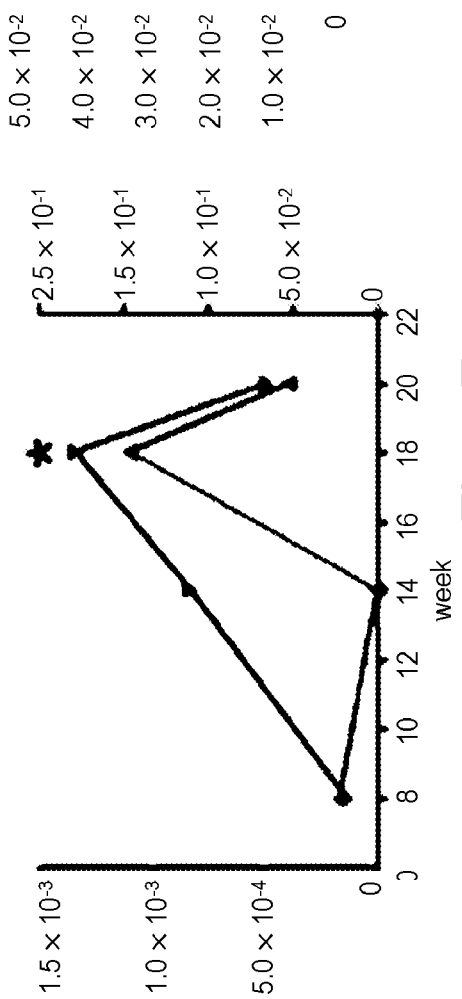

SEQUENCE LISTING

<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Forward Primer for Mouse Amylin Analysis, first
      step PCR

<400> SEQUENCE: 1
tggtagtaat ttttagatgg ataaa                                            25

<210> SEQ ID NO 2

```
<211> LENGTH: 24
<212> TYPE: DNA
<213> ORGANISM: Artificial Sequence
<220> FEATURE:
<223> OTHER INFORMATION: Reverse Primer for Mouse Amylin Analysis, first
      step PCR

<400> SEQUENCE: 2
aaattcccta tttaaatccc ctac                                            24

<210> SEQ ID NO 3
<211> LENGTH: 23
<212> TYPE: DNA
<213> ORGANISM: Artificial Sequence
<220> FEATURE:
<223> OTHER INFORMATION: Hypermethylation-specific nested qRTPCT mouse
      amylin, hypermeth-specific forward primer

<400> SEQUENCE: 3
aaacggaagt gtaatacggt tac                                             23

<210> SEQ ID NO 4
<211> LENGTH: 24
<212> TYPE: DNA
<213> ORGANISM: Artificial Sequence
<220> FEATURE:
<223> OTHER INFORMATION: Hypermethylation-specific nested qRTPCT mouse
      amylin, hypermeth-specific reverse primer

<400> SEQUENCE: 4
ttaccatata tattcgatcc cacg                                            24

<210> SEQ ID NO 5
<211> LENGTH: 23
<212> TYPE: DNA
<213> ORGANISM: Artificial Sequence
<220> FEATURE:
<223> OTHER INFORMATION: Hypermethylation-specific nested qRTPCT mouse
      amylin, hypometh-specific forward primer

<400> SEQUENCE: 5
aaatggaagt gtaatatggt tat                                             23

<210> SEQ ID NO 6
<211> LENGTH: 24
<212> TYPE: DNA
<213> ORGANISM: Artificial Sequence
<220> FEATURE:
<223> OTHER INFORMATION: Hypermethylation-specific nested qRTPCT mouse
      amylin, hypometh-specific reverse primer

<400> SEQUENCE: 6
ttaccatata tattcaatcc caca                                            24

<210> SEQ ID NO 7
<211> LENGTH: 25
<212> TYPE: DNA
<213> ORGANISM: Artificial Sequence
<220> FEATURE:
<223> OTHER INFORMATION: Forward Primer for Human Amylin Analysis, first
      step PCR

<400> SEQUENCE: 7
tgttattagt tattaggtgg aaaag                                           25

<210> SEQ ID NO 8
<211> LENGTH: 25
```

-continued

```
<212> TYPE: DNA
<213> ORGANISM: Artificial Sequence
<220> FEATURE:
<223> OTHER INFORMATION: Reverse Primer for Human Amylin Analysis, first
      step PCR

<400> SEQUENCE: 8
tcttaccata tatattaaat cccac                                            25

<210> SEQ ID NO 9
<211> LENGTH: 25
<212> TYPE: DNA
<213> ORGANISM: Artificial Sequence
<220> FEATURE:
<223> OTHER INFORMATION: Hypermethylation-specific nested qRTPCT human
      amylin, common forward primer

<400> SEQUENCE: 9
tgttattagt tattaggtgg aaaag                                            25

<210> SEQ ID NO 10
<211> LENGTH: 23
<212> TYPE: DNA
<213> ORGANISM: Artificial Sequence
<220> FEATURE:
<223> OTHER INFORMATION: Hypermethylation-specific nested qRTPCT human
      amylin, hypermeth-specific reverse primer

<400> SEQUENCE: 10
taaaaatttt accaaacgct acg                                              23

<210> SEQ ID NO 11
<211> LENGTH: 23
<212> TYPE: DNA
<213> ORGANISM: Artificial Sequence
<220> FEATURE:
<223> OTHER INFORMATION: Hypermethylation-specific nested qRTPCT human
      amylin, hypometh-specific reverse primer

<400> SEQUENCE: 11
taaaaaattt accaaacact aca                                              23

<210> SEQ ID NO 12
<211> LENGTH: 25
<212> TYPE: DNA
<213> ORGANISM: Artificial Sequence
<220> FEATURE:
<223> OTHER INFORMATION: Native Amylin PCR human forward primer

<400> SEQUENCE: 12
tgttaccagt catcaggtgg aaaag                                            25

<210> SEQ ID NO 13
<211> LENGTH: 25
<212> TYPE: DNA
<213> ORGANISM: Artificial Sequence
<220> FEATURE:
<223> OTHER INFORMATION: Native Amylin PCR human reverse primer

<400> SEQUENCE: 13
tcttgccata tgtattggat cccac                                            25

<210> SEQ ID NO 14
<211> LENGTH: 25
<212> TYPE: DNA
<213> ORGANISM: Artificial Sequence
<220> FEATURE:
```

<223> OTHER INFORMATION: Human insulin methylation independent forward
      primer

<400> SEQUENCE: 14
gtgcggttta tatttggtgg aagtt                                          25

<210> SEQ ID NO 15
<211> LENGTH: 30
<212> TYPE: DNA
<213> ORGANISM: Artificial Sequence
<220> FEATURE:
<223> OTHER INFORMATION: Human insulin methylation independent reverse
      primer

<400> SEQUENCE: 15
acaacaataa acaattaact caccctacaa                                     30

<210> SEQ ID NO 16
<211> LENGTH: 16
<212> TYPE: DNA
<213> ORGANISM: Artificial Sequence
<220> FEATURE:
<223> OTHER INFORMATION: Human methylated insulin probe 1

<400> SEQUENCE: 16
acctcccgac gaatct                                                    16

<210> SEQ ID NO 17
<211> LENGTH: 17
<212> TYPE: DNA
<213> ORGANISM: Artificial Sequence
<220> FEATURE:
<223> OTHER INFORMATION: Human methylated insulin probe 2

<400> SEQUENCE: 17
tacctctcgt cgaatct                                                   17

<210> SEQ ID NO 18
<211> LENGTH: 16
<212> TYPE: DNA
<213> ORGANISM: Artificial Sequence
<220> FEATURE:
<223> OTHER INFORMATION: Human insulin demethylated DNA probe 3

<400> SEQUENCE: 18
acctcccaac aaatct                                                    16

<210> SEQ ID NO 19
<211> LENGTH: 17
<212> TYPE: DNA
<213> ORGANISM: Artificial Sequence
<220> FEATURE:
<223> OTHER INFORMATION: Human insulin demethylated DNA probe 4

<400> SEQUENCE: 19
tacctcccat caaatct                                                   17

<210> SEQ ID NO 20
<211> LENGTH: 28
<212> TYPE: DNA
<213> ORGANISM: Artificial Sequence
<220> FEATURE:
<223> OTHER INFORMATION: Outer PCR amplification insulin DNA PCR forward
      primer (Akirav 2011)

<400> SEQUENCE: 20
ttagggtttt taaggtaggg tatttggt          28

<210> SEQ ID NO 21
<211> LENGTH: 37
<212> TYPE: DNA
<213> ORGANISM: Artificial Sequence
<220> FEATURE:
<223> OTHER INFORMATION: Outer PCR amplification insulin DNA PCR reverse
      primer (Akirav 2011)

<400> SEQUENCE: 21
accaaaaaca acaataaaca attaactcac cctacaa          37

<210> SEQ ID NO 22
<211> LENGTH: 26
<212> TYPE: DNA
<213> ORGANISM: Artificial Sequence
<220> FEATURE:
<223> OTHER INFORMATION: Outer PCR amplification methylated insulin DNA
      PCR forward inner primer

<400> SEQUENCE: 22
gtggatgcgt tttttgtttt tgttgg          26

<210> SEQ ID NO 23
<211> LENGTH: 25
<212> TYPE: DNA
<213> ORGANISM: Artificial Sequence
<220> FEATURE:
<223> OTHER INFORMATION: Outer PCR amplification methylated insulin DNA
      PCR reverse inner primer

<400> SEQUENCE: 23
caccctacaa atcctctacc tcccg          25

<210> SEQ ID NO 24
<211> LENGTH: 29
<212> TYPE: DNA
<213> ORGANISM: Artificial Sequence
<220> FEATURE:
<223> OTHER INFORMATION: Outer PCR amplification demethylated insulin
      DNA PCR forward inner primer

<400> SEQUENCE: 24
ttgtggatgt gttttttgtt tttgttggt          29

<210> SEQ ID NO 25
<211> LENGTH: 25
<212> TYPE: DNA
<213> ORGANISM: Artificial Sequence
<220> FEATURE:
<223> OTHER INFORMATION: Outer PCR amplification demethylated insulin
      DNA PCR reverse inner primer

<400> SEQUENCE: 25
caccctacaa atcctctacc tccca          25

<210> SEQ ID NO 26
<211> LENGTH: 17
<212> TYPE: DNA
<213> ORGANISM: Artificial Sequence
<220> FEATURE:
<223> OTHER INFORMATION: Probe for hypomethylated Mouse Amylin DNA

<400> SEQUENCE: 26
aaacgctacg ttacaca          17

```
<210> SEQ ID NO 27
<211> LENGTH: 17
<212> TYPE: DNA
<213> ORGANISM: Artificial Sequence
<220> FEATURE:
<223> OTHER INFORMATION: Probe for hypermethylated Mouse Amylin DNA

<400> SEQUENCE: 27
aaacactaca ttacaca                                                17
```

SYSTEM, METHOD AND KIT FOR ANALYSIS OF CIRCULATING DIFFERENTIALLY METHYLATED DNA AS A BIOMARKER OF BETA-CELL LOSS

CROSS-REFERENCE TO RELATED APPLICATIONS

This application is a U.S. national stage entry under 35 U.S.C. §371 of PCT International Patent Application No. PCT/US2016/041753, filed Jul. 11, 2016, which claims benefit of U.S. Provisional Application No. 62/191,115, filed Jul. 10, 2015, the contents of each of which are incorporated herein by reference into the subject application.

BACKGROUND OF THE INVENTION

Field of the Invention

The present invention relates to the field of epigenetic analysis, and more particularly to the field of differentially methylated gene analysis for determining cell-type specific pathology. More particularly, the present application relates to compositions and methods for assessing particular cell loss by quantitating DNA derived from that particular cell type, with methylation status-specific nucleotide sequences of genes that have unique gene methylation patterns expressed by those cells.

Description of the Art

There are a number of diseases which are characterized by selective cell loss of particular cells. For example, type I diabetes can result from an autoimmune process which targets pancreatic β cells, resulting in loss of this cell type and the insulin they produce. During cell loss, DNA from these cells is released, and some finds its way into the circulating body fluids. Because pancreatic β cells are the only significant cell type which produces significant amounts of insulin, only these cells have demethylated insulin gene DNA. Similarly, in multiple sclerosis, an autoimmune process can lead to loss of oligodendrocytes, which selectively produce myelin oligodendrocyte glycoprotein. The death of oligodendrocytes is therefore associated with an increase in the level of demethylated myelin oligodendrocyte glycoprotein DNA. Other autoimmune diseases are listed in Table 1.

TABLE 1

| Autoimmune Diseases |
|---|
| Acute disseminated encephalomyelitis; Acute motor axonal neuropathy; Addison's disease (Auto-Ab: 21 hydroxylase); Adiposis dolorosa; Adult-onset Still's disease (macrophage migration inhibitory factor. Auto-Ab: ANA); Alopecia Areata (Auto-Ab: T-cells); Ankylosing Spondylitis. CD8; HLA-B27); Anti-Glomerular Basement Membrane nephritis (Auto-Ab: Anti-Basement Membrane Collagen Type IV Protein); Anti-neutrophil cytoplasmic antibody-associated vasculitis (Auto-Ab: Anti-neutrophil cytoplasmic (cANCA)) Anti-N-Methyl-D-Aspartate Receptor Encephalitis; Antiphospholipid syndrome (HLA-DR7, HLA-B8, HLA-DR2, HLA-DR3. Auto-Ab: anti-cardiolipin; anti pyruvate dehydrogenase; β2 glycoprotein I; phosphatidylserine; anti apoH; Annexin A5); Antisynthetase syndrome; Aplastic anemia; Autoimmune Angioedema; Autoimmune enteropathy; Autoimmune hemolytic anemia (complement activation); Autoimmune hepatitis (Auto-Ab: ANA and SMA, LKM-1, LKM-2 or LKM-3; antibodies against soluble liver antigen (anti-SLA, anti-LP) no autoantibodies detected (~20%)); Autoimmune inner ear disease; Autoimmune lymphoproliferative syndrome (TNFRSF6; defective Fas-CD95 apoptosis); Autoimmune neutropenia; Autoimmune Oophoritis; Autoimmune orchitis; Autoimmune pancreatitis (Auto-Ab: ANA; anti-lactoferrin antibodiesanti-carbonic anhydrase antibodies; rheumatoid factor); Autoimmune polyendocrine syndrome; Autoimmune polyendocrine syndrome type 2 (DQ2, DQ8 and DRB1 0404. Auto-Ab: anti-21 hydroxylase, anti-17 hydroxylase); Autoimmune polyendocrine syndrome type 3; Autoimmune progesterone dermatitis; Autoimmune retinopathy; Autoimmune thrombocytopenic purpura (Auto-Ab: anti gpIIb-IIIa or 1b-IX); Autoimmune thyroiditis (HLADR5, CTLA-4. Auto-Ab: antibodies against thyroid peroxidase and/or thyroglobulin); Autoimmune urticaria; Autoimmune uveitis (Auto-Ab: HLAB-27?); Balo concentric sclerosis; Behçet's disease (immune-mediated systemic vasculitis; linkage to HLA-B51 (HLA-B27); very different manifestations with ulcers as common symptom); Bickerstaff's encephalitis (similar to Guillain-Barré syndrome. Auto-Ab: Anti-GQ1b 2/3 patients); Bullous pemphigoid (Auto-Ab: IgG autoantibodies targeting the type XVII collagen component of hemidesmosomes); Celiac disease (HLA-DQ8 and DQ2.5. Auto-Ab: Anti-tissue transglutaminase antibodies anti-endomysial IgA, anti-gliadin IgA); Chronic inflammatory demyelinating polyneuropathy (similar to Guillain-Barré syndrome. Auto-Ab: anti-ganglioside antibodies); Churg-Strauss syndrome (Auto-Ab: p-ANCA Eosinophilia); Cicatricial pemphigoid (precipitates C3. Auto-Ab: anti-BP-1, anti BP-2); Cogan syndrome; Cold agglutinin disease (idiopathic or secondary to leukemia or infection. Auto-Ab: IgM); CREST syndrome (Auto-Ab: Anti-centromere antibodies Anti-nuclear antibodies); Crohn's disease (Innate immunity; Th17; Th1; ATG16L1; CARD15; XBP1;); Dermatitis herpetiformis (Auto-Ab: IgA Eosinophilia; anti-epidermal transglutaminase antibodies); Dermatomyositis (B- and T-cell perivascular inflammatory infiltrate on muscle biopsy. Auto-Ab: histidine-tRNA anti-signal recognition peptide Anti-Mi-2 Anti-Jo1); Diabetes mellitus type 1 (HLA-DR3, HLA-DR4. Auto-Ab: Glutamic acid decarboxylase antibodies (GADA), islet cell antibodies (ICA), and insulinoma-associated autoantibodies (IA-2), anti-insulin antibodies); Discoid lupus erythematosus (IL-2 and IFN-gamma); Drug-induced lupus (Auto-Ab: Anti-histone antibodies); Endometriosis; Enthesitis-related arthritis (MMP3, TRLR2, TLR4, ERAP1. Autoantibodies); Eosinophilic fasciitis; Epidermolysis bullosa acquisita (COL7A1); Erythema nodosum; Essential mixed cryoglobulinemia; Evans syndrome; Felty syndrome; Fibromyalgia; Gestational pemphigoid (Auto-Ab: IgG and C3 misdirected antibodies intended to protect the placenta); Giant cell arteritis; Graves' disease (Auto-Ab: thyroid autoantibodies (TSHR-Ab) that activate the TSH-receptor (TSHR)); Graves ophthalmopathy; Guillain-Barré syndrome (Auto-Ab: Anti-ganglioside, anti-GQ1b); Hashimoto's encephalopathy (Auto-Ab: alpha-enolase); Henoch-Schonlein purpura (Auto-Ab: immunoglobulin A (IgA) and complement component 3 (C3)); Hidradenitis suppurativa; Idiopathic inflammatory |

TABLE 1-continued

Autoimmune Diseases demyelinating diseases (A set of different variants of multiple sclerosis); IgG4-related systemic disease; Inclusion body myositis (Similar to polymyositis but does not respond to steroid therapy-activated T8 cells); Intermediate uveitis; Interstitial cystitis (Mast cells); Juvenile Arthritis (Auto-Ab: inconsistent ANA Rheumatoid factor); Kawasaki's disease (ITPKC HLA-B51); Lambert-Eaton myasthenic syndrome (HLA-DR3-B8. Auto-Ab: voltage-gated calcium channels; Q-type calcium channel, synaptogagmin, muscarinic acetylcholine receptor M1); Leukocytoclastic vasculitis; Lichen planus; Lichen sclerosus; Ligneous conjunctivitis; Linear IgA disease; Lyme disease (Chronic); Ménière's disease (Auto-Ab: major peripheral myelin protein P0); Microscopic colitis; Microscopic polyangiitis (Binds to neutrophils causing them to degranulate and damages endothelium. Auto-Ab: p-ANCA myeloperoxidase); Mixed connective tissue disease (HLA-DR4. Auto-Ab: anti-nuclear antibody anti-U1-RNP); Mooren's ulcer; Morphea; Mucha-Habermann disease (T-cells); Multiple sclerosis, pattern II (Autoantibody against potassium channel has been reported to present demyelination pattern II. Other cases present autoimmunity against MOG and Anoctamin-2. The three reported autoimmune variants belong to MS pattern II. Also involved HLA-DR2, PECAM-1, Anti-myelin basic protein. Auto-Ab: Anti-Kir4.1, Anti-MOG, Anti-ANO2 (heterogeneous)); Myasthenia gravis (HA-B8 HLA-DR3 HLA-DR1. Auto-Ab: nicotinic acetylcholine receptor MuSK protein); Myocarditis; Myositis; Neuromyelitis optica (Auto-Ab: NMO-IgG aquaporin 4); Neuromyotonia (Auto-Ab: Voltage-gated potassium channels); Opsoclonus myoclonus syndrome (Lymphocyte recruitment to CSF); Optic neuritis; Ord's thyroiditis; Oshtoran Syndrome (Heritable, abnormalities in the kynurenine and glutamate metabolism); Palindromic rheumatism (Auto-Ab: anti-cyclic citrullinated peptide antibodies (anti-CCP) and antikeratin antibodies (AKA)); Paraneoplastic cerebellar degeneration (Auto-Ab: anti-Yo (anti-cdr-2 in purkinje fibers) anti-Hu, anti-Tr, antiglutamate receptor); Paroxysmal nocturnal hemoglobinuria; Parry Romberg syndrome (Auto-Ab: ANA); Parsonage-Turner syndrome; Pediatric Autoimmune Neuropsychiatric Disorder Associated with *Streptococcus* (antibodies against streptococcal infection serve as auto-antibodies); Pemphigus vulgaris (Auto-Ab: Anti-Desmoglein 3 eosinophilia); Pernicious anemia (Auto-Ab: anti-parietal cell antibody); Pityriasis lichenoides et varioliformis acuta; Polyarteritis nodosa; Polymyalgia rheumatica; Polymyositis (Auto-Ab: IFN-gamma, IL-1, TNF-alpha); Postmyocardial infarction syndrome (Auto-Ab: myocardial neo-antigens formed as a result of the MI); Postpericardiotomy syndrome; Primary biliary cirrhosis (Auto-Ab: Anti-p62, Anti-sp100, Anti-Mitochondrial(M2)Anti-Ro aka SSA. Note that Sjogren's is classified in some places (e.g., MeSH) as rheumatoid disease, but there is no published evidence to support that classification); Primary sclerosing cholangitis (Possible overlap with primary biliary cirrhosis. Auto-Ab: HLA-DR52a); Progressive inflammatory neuropathy (similar to Guillain-Barré syndrome. Auto-Ab: Anti-ganglioside antibodies: anti-GM1, anti-GD1a, anti-GQ1b); Psoriasis (CD-8 T-cells, HLA-Cw6, IL-12b, IL-23b, TNFalpha, NF-Kb); Psoriatic arthritis (HLA-B27); Pure red cell aplasia; Reactive arthritis; Relapsing polychondritis; Restless leg syndrome (May occur in Sjogren's syndrome, celiac disease, and rheumatoid arthritis or in derangements of iron metabolism); Retroperitoneal fibrosis; Rheumatic fever (Auto-Ab: streptococcal M protein cross reacts with human myosin); Rheumatoid arthritis (HLA-DR4, PTPN22, depleted B cells, TNF alpha, IL-17, (also maybe (IL-1, 6, and 15). Auto-Ab: Rheumatoid factor (anti-IgGFc), Anti-MCV, ACPAs(Vimentin)); Rheumatoid vasculitis (A symptom of Lupus); Sarcoidosis (BTNL2; HLA-B7-DR15; HLA DR3-DQ2); Schnitzler syndrome (IgM?); Scleritis; Sjogren's syndrome (Auto-Ab: anti-Ro. Also, they are often present in Sjogren's syndrome); Stiff person syndrome (GLRA1 (glycine receptor). Auto-Ab: glutamic acid decarboxylase (GAD)); Subacute bacterial endocarditis (Auto-Ab: essential mixed cryoglobulinemia); Susac's syndrome; Sydenham chorea; Sympathetic ophthalmia (Auto-Ab: ocular antigens following trauma); Systemic Lupus Erythematosus (Auto-Ab: Anti-nuclear antibodies anti-Ro. Also, they are often present in Sjogren's syndrome. Eosinophilia); Systemic scleroderma (COL1A2 and TGF-β1. Auto-Ab: anti-nuclear antibodies, anti-centromere and anti-scl70/anti-topoisomerase antibodies); Thrombocytopenia (Multiple mechanisms. Auto-Ab: glycoproteins IIb-IIIa or Ib-IX in ITP anti-ADAMTS13 in TTP. and HUS anti-cardiolipin (anti-cardiolipin antibodies) and β2 glycoprotein I in Antiphospholipid syndrome anti-HPA-1a, anti-HPA-5b, and others in NAIT); Tolosa-Hunt syndrome; Transverse myelitis; Ulcerative colitis; Undifferentiated connective tissue disease (HLA-DR4. Auto-Ab: anti-nuclear antibody); Urticarial vasculitis (Clinically may resemble type I hypersensitivity. Auto-Ab: anti C1q antibodies); Vasculitis (Auto-Ab: sometimes ANCA); Vitiligo (NALP-1 RERE, PTPN22, LPP, IL2RA, GZMB, UBASH3A and C1QTNF6)

Circulating free DNA (cfDNA) can be used for the detection of remote cell loss. For example, in cancer cfDNA is used as a "liquid biopsy" for the detection of tumor growth based on previously documented DNA mutations and epigenetic modifications.

DNA methylation is used by all cells to regulate the expression of tissue specific genes. DNA methylation is a basic mechanism by which cells regulate gene expression, and while all cells share an identical DNA sequence, DNA methylation varies considerably according to cell function. In general, DNA hypermethylation is association with reduced gene expression, while DNA demethylation is association with increased gene expression.

Epigenetic modifications of DNA are used by various cell types to control tissue-specific gene expression. These modifications include histone acetylation/deacetylation and DNA methylation (Klose et al., 2006, Trends Biochem. Sci. 31:89-97; Bartke et al., 2010, Cell 143:470-484; Wang et al., 2007, Trends Mol. Med. 13:373-380). Methylation of DNA sequences occurs in CpG dinucleotide sites to maintain a transcriptionally repressive chromatin configuration, whereas demethylation results in a transcriptionally permissive configuration (Miranda et al., 2007, J. Cell Physiol. 213:384-390). Differential methylation of oncogenes has been used to identify microsatellite instability in patients with colon cancer, detection of differentially methylated DNA in the serum of cancer patients has been used as a biomarker for cancer diagnosis, and beta cell pathology in type I diabetes (Grady et al., 2001, Cancer Res. 61:900-902; Wallner et al., 2006, Clin Cancer Res. 12:7347-7352; Muller et al., 2003, Cancer Res. 63:7641-7645; Akirav, E. M., J. Lebastchi, E. M. Galvan, O. Henegariu, M. Akirav, V. Ablamunits, P. M. Lizardi, and K. C. Herold. 2011. Detection of beta cell death in diabetes using differentially methylated circulating DNA. *Proc Nall Acad Sci USA* 108: 19018-19023). Previous studies have relied on the detection of serum-derived tissue-specific epigenetic modifications to identify DNA released from those cells when they die.

Insulin expression in β-cells is mediated in part by altered DNA methylation. For example, insulin promoter hypomethylation of CpG dinucleotides is detected in insulin positive β-cells, while absent in other tissues. These differential methylation patterns can be detected by bisulfite DNA conversion followed by methylation-specific qRTPCR. Differential methylation of the insulin gene can be used to track the loss of β-cells in patients and animals with T1D, thereby offering a biomarker for the detection of T1D. Differentially methylated insulin DNA may thus be used as a biomarker of β-cell loss in patients and animals with T1D. Examination of β-cell derived insulin cfDNA levels revealed an increase in total β-cell DNA in serum of the non-obese diabetic (NOD) mouse model of T1D and in patients with recent onset type 1 diabetes. However, the presence of β-cell derived insulin cfDNA requires active apoptosis of β-cells, which may not be present during all phases of progression of the disease.

Methylation-specific DNA probes can be used for the detection of β-cell derived insulin DNA. These probes are able to quantitatively and sensitively detect circulation demethylated and methylated insulin DNA from β-cell and non-β-cell origin, respectively. Alternately, methylation specific primers may be employed (see, e.g., Akirav E M, Lebastchi J, Galvan E M, Henegariu O, Akirav M, Ablamunits V, Lizardi P M, and Herold K C. Detection of beta cell death in diabetes using differentially methylated circulating DNA. PNAS, 2011, Proceedings of the National Academy of Sciences, 2011, November:108(19018-23), hereinafter Akirav et al. (2011). See also Husseiny M. I., Kuroda A., Kaye A. N., Nair I., Kandeel F., et al. (2012) Development of a Quantitative Methylation-Specific Polymerase Chain Reaction Method for Monitoring Beta Cell Death in Type 1 Diabetes. PLoS ONE 7(10): e47942. doi:10.1371/journal.pone.0047942), which presented with a relatively low specificity (i.e., demethylated primers detected methylated DNA and vice versa). Low specificity negatively impacts assay sensitivity by decrease detection limits of demethylated DNA. Low DNA levels are presumably present during early cell loss. See, U.S. Pat. No. 6,150,097. Other methods of quantifying nucleic acid sequences, and methylation properties of DNA sequences, are known.

Islet Amyloid Polypeptide (IAPP), also known as amylin, is a gene expressed predominantly in pancreatic β-cells. Amylin is co-secreted with insulin from the secretory granules, and shares similar transcription elements with the insulin gene. The amylin peptide is 37 amino acids in length, and has been identified as the primary component of amyloid deposits observed in the islets of type 2 diabetes (T2D) patients. Amylin secretion has been linked to satiety and inhibition of glucagon secretion. Current therapy for T1D and T2D includes the use of amylin analogs for controlling body weight and lowering blood glucose levels.

Multiple sclerosis (MS) is an autoimmune disease of the central nervous system (CNS) characterized by impaired physical and mental functions. MS can be divided into different disease subtypes all of which display injury of the grey and white matter of the brain, as well as, the spinal cord. Current biomarkers of MS include magnetic resonance imagining and immunological markers, which are used together with clinical symptoms to diagnose the disease. Despite these advancements, recent studies report a relatively high rate of MS misdiagnosis, which may lead to inadequate care. Several cell types affected by MS include neurons, microglia, and oligodendrocytes (ODCs). ODCs, which form the myelin sheath, are targeted directly by immune cells that lead to cell loss. MS is thus another example of a disease characterized by pathology directed at specific types of cells. This loss of ODCs is associated with decrease myelination and impaired nerve cell conductivity and function, while remyelination is often associated with ODC recovery. Myelin oligodendrocyte glycoprotein (MOG), a key component of the myelin sheath, is produced by ODCs and has long been studied as a primary antigen in MS. MOG is predominantly expressed by ODC, making it a good biomarker of ODC loss. ODC loss is observed in nearly all MS disease subtypes. In ODCs, the MOG gene is demethylated (deMeth) while other cells maintain a methylated (Meth) form of the gene. A unique methylation signature is found in myelin producing cells. DNA released from ODCs into the blood during CNS injury is may be detected using methylation specific primers and probes. Abnormal levels of ODC DNA serve as an indication of an ongoing destruction of ODCs in patients with CNS injury.

SUMMARY OF THE INVENTION

Nearly all the cells within higher organisms contain an identical DNA sequence. However, different cells which reside in different tissues may modify the DNA according to their function. Accordingly, DNA in different organs and different cell types bare different signatures.

Sensitive quantitative real time PCR (qRTPCR) of demethylated circulating free insulin DNA can be used as a biomarker of β-cell death in patients with T1D. Similar to insulin, amylin is produced and secreted by β-cells in the islet. However, the demthylated DNA for insulin and amylin genes is not 100% correlated, and changes over stages of pathology. Therefore, assessment of only one such gene does not provide a complete picture of the status of the β-cells. Similarly, in other organs and cell types, use of a single demethylated gene to assess cell pathology may yield incomplete or contradictory results. Therefore, one aspect of the present technology is to employ panels of selected genes, which can then be analyzed together to provide more complete data. Further, while insulin and amylin are believed to be reasonably specific for β-cells, there are conditions, such as endocrinoma, where these hormones may be secreted by other cells. More generally, by employing panels of markers, the use of less specific components is facilitated, since the goal is to assess a pattern of cfDNA and demethylation status, rather than a specific gene status. Of course, each gene may have its own interpretation, especially in the case of insulin and amylin, where non-β-cell expression is rare.

The specific expression of amylin in β-cells, and the differential methylation of the amylin gene in insulinoma cells and primary islets of murine origin, suggest that amylin demethylation can be used as a biomarker of β-cell loss in circulation. Indeed, methylation-specific amylin primers show the ability to detect increased β-cell death in the non-obese diabetic mouse model of T1D and in patients with recent onset T1D. Amylin shows a correlation with insulin cfDNA, providing a multigene gene approach for the detection of β-cell death in T1D. By analyzing multiple genes, the sensitivity and specificity of the analysis can be improved.

Further, the determination of demethylation status of less specific genes for a target condition may improve the information available for monitoring, and may also be useful for screening a population for a number of previously undiagnosed conditions. For example, examination of amylin expression in the islet during T1D progression reveals a disconnect from insulin expression during the late stages of the disease, suggesting that amylin may be used to detect an insulin-negative β-cell fraction that would otherwise go undetected by an insulin-gene-only based biomarker assay. In T1D patients, amylin cfDNA is increased following disease onset demonstrating the utility of this biomarker in human disease.

A method is provided for the detection of extrapancreatic circulating β cell-derived amylin DNA that is indicative of acute and chronic β cell destruction, and thus provides an early biomarker for β cell death in human tissues, serum and other bodily fluids, such as saliva, urine, sweat, tears, and the like, may serve as non-invasive or mildly invasive sources for clinical samples. The method can identify β cell death before the onset of hyperglycemia and diabetes. This strategy may prove useful for monitoring β cell destruction in individuals at risk for the development of diabetes, monitoring the progression of β cell destruction in individuals with diabetes, and use as a marker to guide therapy in patients with diabetes with possible ongoing 13 cell destruction. Similarly, in other diseases characterized by pathology of a single cell types, such as autoimmune diseases (see Table 1), genetic metabolic defects, targeted toxins, targeted injury, and the like, may benefit from the use of the current technology.

In various embodiments, methods of the invention assesses the presence of β cell-derived DNA that is released upon β cell death by using a quantitative PCR or probe technology. The expression of amylin is epigenetically controlled by DNA methylation. By using PCR primers and/or probes and/or other nucleic acid sequence dependent/methylation dependent technologies, such as so-called gene chips, the method permits identification or demethylated amylin and/or insulin DNA patterns that are present only in β cells, distinguished from methylated amylin and/or insulin patterns as are present in other body cells. Therefore, the method provides a bioassay for detecting β cell loss in diabetes to provide a method capable of improving disease diagnosis, allowing for disease staging, and providing a better evaluation of clinical treatment efficacy. In various embodiments of the invention detects β cell loss associated with T1D, T2D, or gestational diabetes, or any combination thereof.

Demethylated circulating free amylin DNA can thus be used as a biomarker of β-cell death in T1D. Amylin DNA shows demethylation patterns within the coding region of the gene in β-cells, and can be specifically distinguished by methylation specific primers or probes. DNA isolated from murine or human pancreas and purified islets shows a strong signal for demethylated amylin DNA by methylation specific qRTPCR. This signal was not detected in other tissues. Increased levels of demethylated amylin DNA were detected in serum of NOD mice during T1D progression and followed the development of hyperglycemia. Similar to mouse, human islets and enriched β-cells yielded a strong qRTPCR signal using methylation sensitive amylin primers. DNA from sera of patients with recent onset T1D showed a high signal for demethylated DNA when compared with matched healthy controls. These findings support the use of demethylated circulating free amylin DNA in identifying β-cell death. When utilized in conjunction with insulin, this assay provides a multi-gene approach towards the detection of β-cell loss.

The amylin gene is differentially methylated in primary islets and murine insulinomas, and can be detected by methylation-specific primers. Insulin gene regulation is mediated, in part, by DNA methylation of the insulin promoter and coding sequences. Amylin is expressed predominantly by β-cells and secreted together with insulin, therefore suggesting that amylin DNA may be uniquely demethylated in these cells. Analysis of methylation in the amylin gene coding region revealed several unique demethylated patterns in β-cells when compared with other murine and human tissues. Similar methylation patterns were also found in insulinoma cells, suggesting that amylin regulation may be controlled, in part, by DNA modification. The presence of β-cell specific methylation patterns in the amylin gene provide an opportunity to employ methylation-specific primers capable of distinguishing between β-cell derived DNA (demethylated DNA) and DNA from all other tissues (methylated DNA).

Sequence analysis of bisulfate-converted DNA from murine brain, kidney, liver, small intestine and stomach revealed a complete methylation of CpG dinucleotides in the coding region of the amylin gene. In contrast, sequence analysis of DNA from murine pancreas and purified islets revealed a mixed population of C/T nucleotides post bisulfite conversion suggesting that the amylin gene is demethylated in β-cells. Finally, analysis of amylin methylation in βTC3 murine insulinomas showed demethylation of CpG dinucleotides when compared with the murine islet-derived endothelial cell line, MS1.

Methylation sensitive primers for both murine and human amylin sequence showed a high degree of specificity and sensitivity when tested on artificially methylated and demethylated DNA throughout a wide range of the DNA concentrations. Moreover, analysis of DNA from islets shows a high DMI when compared with other tissues. Similar results were also observed when DNA extracted from human islets or enriched β-cells were compared to human liver.

The designed methylation-specific primers allowed detection of demethylated DNA in the NOD mouse model of T1D. Demethylated amylin DNA levels showed increases in prediabetic NOD mice reaching a peak at disease presentation. This increase in demethylated DNA, which may represent an increase in overall β-cell loss, was independent of any changes in total DNA concentration in the blood of these mice, indicating that the chronic nature of autoimmune T1D does not lead to an overall increase in cfDNA in the blood. On a single animal level, DMI values revealed a high degree of variability in demethylated amylin DNA. Such variability in β-cell loss is in agreement with the desynchronized nature of disease onset in this spontaneous model of T1D. Demethylated amylin DNA may be as a biomarker of diabetes progression in the NOD mouse.

The human amylin coding region shares a high degree of sequence homogeneity with the mouse. Therefore, homologous sequences in the human amylin gene to those of mouse gene that also exhibited differential methylation were identified. Synthesis of methylation-specific human amylin primers showed a high degree of specificity and sensitivity to artificially demethylated DNA as well as DNA from primary human islets and enriched β-cells. Methylation-specific primers showed a statistically significant increase in amylin cfDNA in RO T1D patients when compared with unrelated HC. Assay performance showed good specificity and sensitivity by Receiver Operating Characteristic (ROC)

analysis. Moreover, the tendency towards a correlation between DMI HbA1c values may suggest that diabetes severity due to poor metabolic control and associated immune activation may contribute to β-cell loss. Lastly, DMI values of insulin cfDNA were in overall agreement with amylin DMI values. The combination of both insulin and amylin DMI offers an opportunity for a dual-gene approach to measure β-cell loss. This dual-gene assay can enhance assay validity and reliability by expanding assay measurement to more than a single gene for β-cell loss detection.

The amylin gene in the islet and enriched β-cells is differentially methylated, and provides an opportunity to detect the presence of β-cell derived demethylated amylin cfDNA by using methylation-specific primers. Amylin can be used as a secondary gene to detect β-cell death in recent onset T1D patients in conjunction with the insulin gene. A two gene assay for (3-cell loss can provide a risk index for better assay reliability and validity.

Other genes have been correlated with aspects of diabetes, and therefore present additional opportunities for establishing an epigenetic panel of tests.

The treatment of double-stranded genomic DNA with sodium bisulfate leads to the deamination of unmethylated cytosine residues into uracil residues, and to the formation of two single strands that are no longer complementary. During this treatment, 5-methyl cytosine is maintained. The differences in sequence produced in this way form the basis of the differentiation between methylated and unmethylated DNA (Frommer, Proc. Natl. Acad. Sci. 889 (1992), 1827-1831). DNA treated with bisulfite can be used directly in PCR in which uracil residues (previously unmethylated cytosine) and thymidine residues are amplified as thymidine and only 5-methylcytosine residues are amplified as cytosine residues. Depending on the application, the primers used for the PCR differentiate between methylated and unmethylated sequences or amplify fragments independently of the methylation status. PCR fragments which have been amplified using non-discriminating primers can, for instance, be sequenced directly to determine the proportion of methylated and unmethylated CpGs. Other methodical approaches utilize the differences in sequence for the specific amplification of methylated and unmethylated sequences by discriminating primers or probes (methylation-specific PCR, methylight PCR) (Dahl (2003), loc. cit.). Bisulfite-inducing differences in sequence of PCR products can also be found by means of methylation-specific oligonucleotide (MSO) micro-arrays (Shi, J. Cell. Biochem. 88 (2003), 138-143; Adorjan, Nucleic Acid Res. 30 (2002), e21; Gitan, Genome Res. 12 (2002), 158-164). In contrast to the methylation-sensitive restriction enzymes, the DNA treated with bisulfite can provide information on the methylation status of several CpG residues in an amplified genomic fragment. The treated DNA is not suitable for analyses throughout the genome presumably due to its reduced complexity and its high degree of denaturation.

Methylated DNA fragments may be enriched by affinity chromatography (Cross, Nat. Genet.6 (1994), 236-244). A recombinant MECP2 bound to a matrix was used for binding the methylated DNA. See also (Shiraishi, Proc. Natl. Acad. Sci. 96 (1999), 2913-2918; Brock, Nucleic Acid. Res. 29 (2001), E123). The binding of strongly or less strongly methylated genomic sequences to an affinity matrix depends on the salt concentration which makes it possible to separate the CpG islands with dense methylation from other sequences with a lower methylation density.

A polynucleotide having a nucleotide sequence encoding a bifunctional polypeptide comprising the DNA-binding domain of a protein belonging to the family of Methyl-CpG binding proteins (MBDs) and an Fc portion of an antibody may be provided. See, U.S. Pat. No. 9,074,013. The bifunctional polypeptide may further include a nucleotide sequence encoding a linker polypeptide. The polypeptide may contain a protease cleavage site (e.g., thrombin) preceding the Fc portion which cleavage of the Fc portion. A recombinant methyl-CpG-binding, antibody-like protein can preferentially bind CpG methylated DNA in an antibody-like manner That means, the methyl-CpG-binding, antibody-like protein has a high affinity and high avidity to its antisense sequence, which is preferably DNA that is methylated at CpG dinucleotides. The antibody-like structure caused by the intermolecular interaction of the constant regions brings the methyl-DNA-binding domain of one polypeptide in close proximity to the methyl-DNA-binding domain of another polypeptide. This allows bivalent interactions between the methyl-DNA-binding proteins and methylated DNA. Accordingly, the polypeptide is capable of binding to its antigen via two methyl DNA-binding domains which are part of the polypeptide. These bifunctional peptides may be made specific for certain sequences, and different bifunctional peptides may be formed in an array, to specifically detect a large number of methylated DNA sequences. The corresponding unmethylated sequences may be detected traditionally, with the difference between total and methylated representing the demethylated portion. Thus, a direct assay for methylated DNA is provided, and this assay can scale to a plurality of genes or DNA sequences, which may advantageously be provided in a single "lab on a chip".

The antibody fragment Fc may be generated in classical manner, such as development of a monoclonal antibody to the DNA sequence, and then sequencing the monoclonal antibody to determine the Fc sequence. Alternately, the Fc may be developed combinatorially using computer models of DNA binding, with the resulting Fc candidates tested for selectivity and specificity in order to choose the best Fc or group of Fc. In some cases, other binding moieties other than Fc may be used. One advantage of using Fc is that a substrate imprinted with a predetermined pattern (e.g., 2D array) of plurality of traditional antigens corresponding to a plurality of Fc fragments may be provided, which then self-assembles when immersed into a mixed solution of the bifunctional peptides or maintains pattern boundaries. Such a substrate can handle hundreds or thousands of different bifunctional peptides. The binding of the bifunctional peptide to a corresponding "antigen" DNA may be detected by use of various enzymes, prosthetic groups, fluorescent materials, luminescent materials, bioluminescent materials, radioactive materials, positron emitting metals using various positron emission topographies, and nonradioactive paramagnetic metal ions. The detectable substance may be coupled or conjugated either directly to an Fc portion of an antibody (or fragment thereof) or indirectly, through an intermediate (such as, for example, a linker known in the art) using techniques known in the art. See, for example, U.S. Pat. No. 4,741,900 for metal ions which can be conjugated to an Fc portion of antibodies for use as diagnostics. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, or $^{99}$Tc. Spectrographic or fluorographic detection is preferred. The substrate may be a pattered semiconductor (e.g., silicon) wafer with detection electronics embedded. Therefore, if the binding of DNA to the bifunctional peptide results in a change in electrochemical potential or a redox reaction, for example, a direct readout in real time is possible. The bifunctional peptide may be attached to solid supports, which are particularly useful for immunoassays or purification of the target antigen. Such solid supports include, but are not limited to, glass, silicon, cellulose, polyacrylamide, nylon, polycobonate, polystyrene, polyvinyl chloride or polypropylene or the like. Techniques for conjugating coupling or linked compounds to the Fc portion are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoelonal Antibodies For Cancer Detection And Therapy, Baldwin et al. (eds.), pp. 303-16 (Academic Press 1985), and Thorpe, Immunol. Rev., 119-158.

The term "DNA-binding domain of a protein belonging to the family of Methyl-CpG binding proteins (MBDs)" encompasses a polypeptide which has preferably the structural and/or functional characteristics of the methyl-DNA-binding domain of a protein of the MBD family which comprises the proteins MeCP2, MBD1, MBD2, MBD3 and MBD4. The methyl-DNA-binding activity can be tested by methods known in the art. Preferably, the term "methylated DNA" encompasses methylated DNA, more preferably, CpG methylated DNA including hemi-methylated or DNA methylated at both strands or single-stranded, methylated DNA. The most important example to date is methylated cytosine that occurs mostly in the context of the dinucleotide CpG, but also in the context of CpNpG- and CpNpN- sequences. In principle, other naturally occurring nucleotides may also be methylated. The polypeptide may bind methylated DNA either as a monomer or dimer or multivalent molecule. It is preferably capable of binding to highly methylated DNA or low methylated DNA. Preferably, it can bind single methylated CpG pairs. An MBD or fragment thereof preferably a methyl-DNA-binding domain or fragment thereof can, for example, be identified by using sequence comparisons and/or alignments by employing means and methods known in the art, and comparing and/or aligning (a) known MBD(s) to/with a sequence suspected to be an MBD. The polypeptide is preferably bifunctional and harbors preferably two methyl-DNA-binding domains as described above, wherein preferably both methyl-DNA-binding domains are able to bind single methylated CpG pairs. The methyl-DNA-binding domain of the polypeptide is, for example, that of human MBD2.

A method is provided for the detection of β-cell-derived DNA that is indicative of acute and chronic β-cell destruction, and thus provides an early biomarker for β-cell death in human tissues, serum and other bodily fluids, and/or a biomarker for monitoring treatment and progression of the disease. The method can identify β-cell death before the onset of diabetes. This strategy may prove useful for monitoring β-cell destruction in individuals at risk for the development of diabetes, monitoring the progression of β-cell destruction in individuals with diabetes, and use as a marker to guide therapy in patients with diabetes with possible ongoing β-cell destruction.

The present technology is not limited to detection, prognosis and treatment of diabetes, and in fact is applicable to other pathology that causes apoptosis of β-cells or other specific cell types. Therefore, when considering test results, such other conditions would generally be included in the differential diagnosis. However, when a patient is tested after revealing a constellation of symptoms that clinically correlate with diabetes, that diagnosis is likely.

The technology relates systems, methods and kits for determining the presence of hypomethylated β-cell DNA in body fluids of a subject which are indicative of β-cell death. Thus, in one embodiment, the invention provides a method of detecting hypomethylated β-cell amylin DNA in a biological sample of a subject including the steps of: obtaining a biological sample from the subject containing β-cell Amylin DNA; determining the methylation status of at least one of the CpG dinucleotides in the β-cell Amylin DNA, where when at least one of the CpG dinucleotides in the β-cell Amylin DNA is determined to be unmethylated, the hypomethylated β-cell Amylin DNA is detected. Likewise, insulin DNA can be determined. When both tests are performed, they provide a panel, optionally with determination of other genes and/or demethylated genes, for assessing state, stage and progression of pathology.

As used herein, "hypomethylated" means that the extent of methylation of a target nucleic acid (such as genomic DNA) is lower than it could be (i.e., a DNA or DNA fragment in which many or most of the CpG dinucleotides are not methylated). By way of a non-limiting example, a hypomethylated nucleic acid is a nucleic acid that is less methylated than it could be, because less than all of the potential methylation sites of the nucleic acid are methylated. By way of another non-limiting example, a hypomethylated nucleic acid, such as in the Amylin gene, is a nucleic acid that is less methylated in a cell type that expresses the nucleic acid (e.g., β-cells), as compared with a cell type that does not express the nucleic acid (e.g., liver cell). A hypomethylated β-cell Amylin DNA may have less than all of the potential methylation sites methylated and is less methylated as compared with a liver cell Amylin DNA.

In another embodiment, a method is provided for detecting β-cell death by detecting hypomethylated β-cell Amylin DNA in a subject, where when at least one of the CpG dinucleotides in the β-cell Amylin DNA is determined to be unmethylated, β-cell death is detected. In a further embodiment, a method is provided for measuring the level of β-cell death by detecting hypomethylated β-cell Amylin DNA in a subject, where the amount of hypomethylated β-cell Amylin DNA is quantified, and where a higher amount of hypomethylated β-cell Amylin DNA indicates a higher level of β-cell death.

In one embodiment, a method is provided for diagnosing a subject with a disease or disorder associated with β-cell death by detecting hypomethylated β-cell Amylin DNA, where when hypomethylated β-cell Amylin DNA is detected, a disease or disorder associated with β-cell death in the subject is diagnosed. In various embodiments, the disease or disorder diagnosable by the methods of the invention includes diabetes.

In another embodiment, a method of assessing the severity of a disease or disorder associated with β-cell death in a subject is provided by detecting hypomethylated β-cell Amylin DNA, where the amount of hypomethylated β-cell Amylin DNA is quantified, and where a higher quantity of hypomethylated β-cell Amylin DNA indicates a greater severity of the disease or disorder in the subject.

In a further embodiment, a method is provided for monitoring the progression of a disease or disorder associated with β-cell death in a subject by detecting hypomethylated β-cell Amylin DNA in the subject, where when the amount of hypomethylated β-cell Amylin DNA detected at a first time point is different than the amount of hypomethylated β-cell Amylin DNA detected at a second time point, the difference in the amount of hypomethylated β-cell Amylin DNA is an indicator of the progression of the disease or disorder associated with β-cell death in the subject.

In one embodiment, a method of monitoring the effect of a therapeutic regimen on a disease or disorder associated with β-cell death in a subject is provided by detecting hypomethylated β-cell Amylin DNA in the subject, where when the amount of hypomethylated β-cell Amylin DNA detected before therapeutic regimen is applied is different than the amount of hypomethylated β-cell Amylin DNA detected during or after the therapeutic regimen is applied, the difference in the amount of hypomethylated β-cell Amylin DNA is an indicator of the effect of the therapeutic regimen on the disease or disorder associated with β-cell death in the subject.

In one embodiment, a kit is provided for detecting hypomethylated β-cell Amylin DNA in a biological sample, comprising asset of primers for selectively amplifying bisulfite-treated methylated and hypomethylated Amylin DNA. A similar kit may be provided for insulin, or for insulin and amylin. Quantitative PCR may be conducted using the primers, and/or a set of probes provided for quantifying an amount of amplified methylated and hypomethylated DNA.

In another embodiment, a composition comprising a biomarker is provided, where the biomarker comprises an isolated hypomethylated β-cell Amylin DNA, or fragment thereof, where the isolated hypomethylated β-cell Amylin DNA was isolated from a biological sample.

In a further embodiment, a composition is provided comprising an amplicon, where the amplicon was produced by PCR using at least one primer that hybridizes to a template comprising an isolated hypomethylated β-cell Amylin DNA, or fragment thereof, where the isolated hypomethylated β-cell Amylin DNA was isolated from a biological sample.

The presence of hypomethylated β-cell DNA, and preferably DNA corresponding to the Amylin gene from those cells, is indicative of β-cell death. For example, cerebrospinal fluid, plasma, serum, urine, saliva, and lymphatic fluid typically do not contain demethylated DNA corresponding to the Amylin gene, and therefore these fluids may be collected and tested, with a low threshold demethylation index for normal individuals. Thus, compositions and methods are provided that may be useful for assessing the extent of methylation of β-cell DNA, for detecting the presence of hypomethylated β-cell DNA as an indicator of β-cell death, for assessing the level of hypomethylated β-cell DNA as a measure of β-cell death, for diagnosing a disease or disorder associated with β-cell death, for monitoring the progression of a disease or disorder associated with β-cell death, for assessing the severity of a disease or disorder associated with β-cell death, for selecting a treatment regimen to treat a disease or disorder associated with β-cell death, and for monitoring the effect of a treatment of a disease or disorder associated with β-cell death.

It is an advantage that β-cell death can be detected non-invasively or minimally invasively, and earlier in the pathological process than other available methods for detecting diseases and disorders associated with β-cell death and early in the progression of diabetes, thereby allowing for earlier diagnosis and therapeutic intervention of the pathologic process.

In one embodiment, the presence of hypomethylated β-cell specific DNA is detected in a biological sample obtained from a subject. The DNA is preferably circulating DNA (cfDNA). In some embodiments, the biological sample is a bodily fluid. In certain embodiments, the biological sample is blood, serum, or plasma. Urine, sweat, tears, and saliva are also possible sources of the DNA sample.

In one embodiment, the hypomethylated β-cell DNA is at least some portion of the Amylin gene DNA. In various embodiments, the hypomethylated Amylin DNA is hypomethylated within at least one of a regulatory region, an intron, an exon, a non-coding region, or a coding region.

In various embodiments, the extent of methylation is assessed using methylation-specific PCR, a methylation-specific DNA microarray, bisulfite sequencing, pyrosequencing of bisulfite treated DNA, or combinations thereof. Information obtained (e.g., methylation status) can be used alone, or in combination with other information (e.g., disease status, disease history, vital signs, blood chemistry, etc.) from the subject or from the biological sample obtained from the subject.

In one embodiment, the detected hypomethylated β-cell DNA is at least some fragment of the Amylin gene. In various embodiments, the detected hypomethylated Amylin DNA is hypomethylated within at least one of a regulatory region, an intron, an exon, a non-coding region, or a coding region. In some embodiments, the extent of methylation of the detected hypomethylated β-cell Amylin gene DNA is compared with the extent of methylation of the Amylin gene DNA of a comparator cell type which does not express Amylin. Non-limiting examples of comparator cell types useful in the methods of the invention include liver cells and kidney cells. In various embodiments, the hypomethylated β-cell DNA is detected using methylation-specific PCR, a methylation-specific DNA microarray, bisulfite sequencing, pyrosequencing of bisulfite treated DNA, antibodies, MBD proteins, other specific binding peptides, bifunctional peptides, or combinations thereof. In one embodiment, the biological sample is a bodily fluid. In various embodiments, the biological sample is at least one of plasma, serum or blood. In some embodiments, the amount of hypomethylated β-cell DNA detected is compared with a comparator, such as a negative control, a positive control, an expected normal background value of the subject, a historical normal background value of the subject, an expected normal background value of a population that the subject is a member of, or a historical normal background value of a population that the subject is a member of. Information obtained from the methods of the invention described herein (e.g., methylation status) can be used alone, or in combination with other information (e.g., disease status, disease history, vital signs, blood chemistry, etc.) from the subject or from the biological sample obtained from the subject.

Information obtained from the methods described herein can be stored in a computerized database associated with an automated processor (microprocessor) run in accordance with computer readable instructions stored on a non-transitory computer readable medium, that can be used for the analysis, diagnosis, prognosis, monitoring, assessment, treatment planning, treatment selection and treatment modification of diseases and disorders associated with β-cell death. Thus, the invention also includes such databases and their methods of use, as well as computer readable media containing instructions for controlling an automated processor to perform the various methods of the invention, data analysis, and produce outputs.

A biological sample can be obtained by appropriate methods, such as, by way of example, biopsy or fluid draw. In certain embodiments, a biological sample containing genomic DNA is used. The biological sample can be used as the test sample; alternatively, the biological sample can be processed to enhance access to nucleic acids (e.g., nucleic acids comprising methylated or unmethylated nucleotides), or copies of nucleic acids (e.g., copies of nucleic acids comprising methylated or unmethylated nucleotides), and the processed biological sample can then be used as the test sample. For example, in various embodiments, nucleic acid is prepared from a biological sample. Alternatively, or in addition, an amplification method can be used to amplify nucleic acids comprising all or a fragment of the nucleic acid in a biological sample, for use as the test sample in the assessment for the presence or absence of methylation.

There are many methods known in the art for the determination of the methylation status of a target nucleic acid. In some embodiments, hybridization methods, such as Southern analysis, can be used (see Current Protocols in Molecular Biology, 2012, Ausubel, F. et al., eds., John Wiley & Sons, including all supplements). For example, methylation-specific restriction enzymes can be used to digest DNA, cleaving at specific sites depending upon methylation status, followed by hybridization with a nucleic acid probe. A "nucleic acid probe," as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc. For representative examples of use of nucleic acid probes, see, for example, U.S. Pat. Nos. 5,288,611 and 4,851,330. See also, Rapley and Harbron, 2011, Molecular Analysis and Genome Discovery, John Wiley & Sons; Tollefsbol, 2010, Handbook of Epigenetics: The New Molecular and Medical Genetics, Academic Press. For example, direct sequence analysis can be used in the methods of the invention to detect the methylation status of a target nucleic acid. For example, bisulfite-treated DNA utilizing PCR and standard dideoxynucleotide DNA sequencing can directly determine nucleotides that are resistant to bisulfite conversion. (Frommer et al., 1992, PNAS 89:1827-1831). Briefly, in an example direct sequencing method, primers are designed that are strand-specific as well as bisulfite-specific (e.g., primers containing non-CpG cytosines so that they are not complementary to non-bisulfite-treated DNA), flanking the potential methylation site. Such primers will amplify both methylated and unmethylated sequences. Pyrosequencing can also be used in the methods of the invention to detect the methylation status of a target nucleic acid. Briefly, in an example pyrosequencing method, following PCR amplification of the region of interest, pyrosequencing is used to determine the bisulfite-converted sequence of specific CpG dinucleotide sites in the target nucleic. (Tost et al., 2003, BioTechniques 35:152-156; Wong et al., 2006, 41:734-739).

A microarray methylation assay can also be used to detect the methylation status of a target nucleic acid. Briefly, target nucleic acids are treated with bisulfite, amplified, hybridized to probes, labeled and detected. (Wang and Petronis, 2008, DNA Methylation Microarrays: Experimental Design and Statistical Analysis; Weisenberger et al., 2008, Comprehensive DNA Methylation Analysis on the Illumina Infinium Assay Platform). For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. Nos. 5,143,854, 5,424,186, No. 5,384, 261, WO90/15070 and WO92/10092. These arrays can generally be produced using mechanical synthesis methods or light directed synthesis methods which incorporate a combination of photolithographic methods and solid phase oligonucleotide synthesis methods. (Fodor et al., Science, 251:767-777 (1991).

Methylation specific PCR can also be used to detect the methylation status of a target nucleic acid. Briefly, sets of PCR primers are designed that will hybridize specifically to either methylated nucleotides or unmethylated nucleotides, after their modification by bisulfite treatment. (Yuryev, 2007, PCR Primer Design, Volume 402, Chapter 19, Humana Press; Esteller, 2005, DNA Methylation: Approaches, Methods, and Applications, CRC Press). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

A preferred probe for detecting DNA is a labeled nucleic acid probe capable of hybridizing to target DNA. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target DNA. Preferably, a probe is less than 25 nucleotides in length. The hybridization sample is maintained under conditions which are sufficient to allow specific hybridization of the nucleic acid probe to DNA. Specific hybridization can be performed under high stringency conditions or moderate stringency conditions, as appropriate. In a preferred embodiment, the hybridization conditions for specific hybridization are high stringency. Specific hybridization, if present, is then detected using standard methods. More than one nucleic acid probe can also be used concurrently in this method. Specific hybridization of any one of the nucleic acid probes is indicative of the presence of the target DNA of interest.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a target nucleic acid sequence. Hybridization of the PNA probe to a target nucleic acid sequence is indicative of the presence of the target nucleic acid.

In another embodiment, analysis by methylation sensitive restriction enzymes can be used to detect the methylation status of a target nucleic acid, if the methylation status results in the creation or elimination of a restriction site. A sample containing nucleic acid from the subject is used. Restriction Fragment Length Polymorphism (RFLP) analysis is conducted as described (see Current Protocols in Molecular Biology, supra). The digestion pattern of the relevant fragments indicates the presence or absence of methylation.

In PCR, the nucleic acid probe can be labeled with a tag as discussed before. Most preferably the detection of the duplex is done using at least one primer directed to the target nucleic acid. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers. Amplification may then be performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

The process for determining the quantitative and qualitative profile may provide real-time DNA amplifications performed using a labeled probe, preferably a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes is the Tm, which is in the range of about 65° C. to 75° C. Preferably, the Tm for any one of the hydrolysis-probes is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

Preferably, a primer nucleotide sequence is sufficiently complementary to hybridize to a nucleic acid sequence of about 12 to 25 nucleotides. More preferably, the primer differs by no more than 1, 2, or 3 nucleotides from the target flanking nucleotide sequence In another aspect, the length of the primer can vary in length, preferably about 15 to 28 nucleotides in length (e.g., 15, 16, 17, 18, 19, 20, 21, 22, 23, 24, 25, 26, 27, or 28 nucleotides in length).

A target nucleic acid, and PCR or other appropriate methods can be used to amplify all or a fragment of the nucleic acid, and/or its flanking sequences, if desired. The methylation status of the nucleic acid, or a fragment thereof (e.g., one or more exons, one or more introns, one or more intragenic regions, one or more regulatory regions, etc.), is determined, using methods elsewhere described herein or otherwise known in the art. The technique used to determine the methylation status of the target nucleic acid can vary in the methods of the invention, so long as the methylation status of the target nucleic acid is determined. In various embodiments of the invention, the methylation status of a target nucleic acid is compared with the methylation status of a comparator nucleic acid.

The probes and primers can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{32}$S or $^{3}$H. The nonradioactive entities are selected from ligands such as biotin, avidin, streptavidin or digoxigenin, haptens, dyes, and luminescent agents such as radioluminescent, chemoluminescent, bioluminescent, fluorescent or phosphorescent agents.

Nucleic acids can be obtained from the biological sample using known techniques. The nucleic acid can be double-stranded or single-stranded (i.e., a sense or an antisense single strand) and can be complementary to a nucleic acid encoding a polypeptide. The nucleic acid content may also be a DNA extraction performed on a fresh or fixed biological sample.

Routine methods also can be used to extract genomic DNA from a biological sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.). The invention also includes compositions comprising amplicons produced by the methods described elsewhere herein using as a template the hypomethylated β-cell DNA comprising at least some portion of Amylin gene DNA, which was isolated from a biological sample. In some embodiments, the hypomethylated β-cell DNA used as a template to produce the amplicons is treated with bisulfite. In some embodiments, the hypomethylated β-cell Amylin DNA used as template to produce the amplicons is unmethylated on at least one of the CpG dinucleotides at β-cell-specific nucleotide positions of the human Amylin gene. In some embodiments, the amplicons of the invention are produced in PCR reaction.

The present invention also pertains to kits useful in the methods of the invention described elsewhere herein. Such kits comprise components useful in any of the methods described herein, including for example, hybridization probes or primers (e.g., labeled probes or primers), reagents for detection of labeled molecules, restriction enzymes, allele-specific oligonucleotides, means for amplification of a subject's nucleic acid (as described elsewhere herein), means for analyzing a subject's nucleic acid (as described elsewhere herein), negative comparator standards, positive comparator standards, and instructional materials. For example, in one embodiment, the kit comprises components useful for analysis of the methylation status of nucleic acids in a biological sample obtained from a subject. A kit may also include instructional materials describing the use of the reagents and devices. A kit may also be associated with computer readable instructions for controlling an automated apparatus to perform the methods and analysis according to various teachings hereof.

A variety of kits having different components are contemplated. Generally, the kit comprises a component for detecting or quantifying methylation status of a nucleic acid obtained from the subject. In another embodiment, the kit comprises a component for collecting a biological sample, such as bodily fluid, from the subject. In another embodiment, the kit comprises instructions for use of the kit contents.

In one embodiment, the kit comprises a means to detect the methylation status of a hypomethylated β-cell DNA. In another embodiment, the kit comprises a means to quantify the level of hypomethylated β-cell DNA present in the subject (as described elsewhere herein).

In various embodiments, methods of the invention assess the presence of β-cell-derived DNA that is released upon β-cell death by using a quantitative probe technology in a traditional PCR assay. By using probes, the method permits one to identify demethylated Amylin DNA patterns that are uniquely or quasi-uniquely present only in β-cells. Therefore, the method provides a bioassay for detecting β-cell loss in neurodegenerative disease such as diabetes, to provide a method capable of improving disease diagnosis, allowing for disease staging, and providing a better evaluation of clinical treatment efficacy.

The method as disclosed herein uses a stepwise detection and analysis of β-cell and non-β-cell derived Amylin DNA. The key principle behind the method is the existence of unique DNA methylation patterns in the β-cells that are absent from other cells in the body. That is, the β-cell DNA methylation pattern associated with the Amylin gene is reasonably unique, and the level of β-cell-origin Amylin gene DNA in the serum and other body fluids is altered by β-cell death or pathology.

By first conducting a bisulfate conversion of DNA extracted from a bodily fluid of an individual, it becomes possible to quantify the relative abundance of β-cell Amylin DNA in the circulation or other body fluids, and hence whether that individual is experiencing β-cell loss.

According to another embodiment, a pattern of gene methylation from a particular cell, even absent uniqueness of demethylation of any particular gene, may be analyzed, by looking for quantitative correlations of demethylated gene DNA in the body fluid. For example, if one considers that certain demethylated genes may be rare in the organism as a whole, but not unique for any particular cell type, when taken as a group, concentrations of a set of rare demethylated gene DNA may provide a reliable indication of a particular cell type of origin, using statistical methods such as principal component analysis. See, US Patent Application Nos. 20090047269; 20090123374; 20090234202; 20090264306; 20100009905; 20100086523; 20100273258; 20110003707; 20110053164; 20110166059; 20120232016; 20130035374; 20130035864; 20130052238; 20130136722; 20130218474; 20130260390; 20130261009; 20130305415; 20140031308; 20140127716; 20140137274; 20140141986; 20140147932; 20140148350; 20140170663; 20140189903; 20140199273; 20140271455; 20140274767; 20140315301; 20150052630; 20150099811; 20150119350; 20150164952; 20150285802; 20150292029; 20150298091; 20150299791; 20150301055; and PCT Pub. Nos. WO2007050706; WO2007112330; WO2008095050; WO2009026152; WO2009126380; WO2010020787; WO2010029167; WO2010123354; WO2010124207; WO2010144358; WO2011133288; WO2011133935; WO2011141711; WO2011157995; WO2012024543; WO2012033537; WO2012047899; WO2012071469; WO2012115885; WO2012122236; WO2013017701; WO2013091074; WO2013148147; WO2013159103; WO2014071281; WO2014081987; WO2014082067; WO2014094043; WO2014133194; WO2014174470; WO2014183122; WO2014184199; WO2014186394; WO2015006590; WO2015006645; WO2015006811; WO2015020929; WO2015048852; WO2015120382; WO2015138870; WO2015153679; and WO2015164212. After the demethylated genes are selected that provide the highest correlation with a particular disease or disorder, these may be typically be used without revalidation across a population. Likewise, absence or low levels of demethylated genes may be indicative of absence of cell death of the particular cell type of interest. When screening a large number of genes, a gene array "chip" or digital PCR or digital droplet PCR technologies may be used. See, US Pat. Pubs. 20090155791;

20110124518; 20110165567; 20130210011; 20130323728; 20140031257; 20140080715; 20140113290; 20140178348; 20150004602; 20150004610; 20150011403; 20150307946; 20150307919; 20150080235, and PCT Pub. Nos. WO2009092035; WO2012052844; WO2012054730; WO2012120374; WO2012162660; WO2013090588; WO2013135454; WO2014043763; WO2014080017; WO2014184684; WO2014189787; WO2014207170; and WO2015048665.

A method is developed for detecting β-cell death in vivo by amplifying regions of genes that: i) are expressed in β-cells (e.g., Amylin); and ii) contain CpG methylation sites, and then measuring the proportion of β-cell-derived DNA in the serum or other body fluids. Generally, by using probes that are specific for DNA methylation patterns in β-cells, circulating copies of β-cell-derived demethylated DNA are detected after bisulfite treatment and PCR amplification. See, Darst R P, Pardo C E, Ai L, Brown K D, Kladde M P; "Bisulfite sequencing of DNA", Curr Protoc Mol Biol. 2010 July; Chapter 7: Unit 7.9.1-17. doi: 10.1002/0471142727.mb0709s91; "Methylation Analysis by Bisulfite Sequencing: Chemistry, Products and Protocols from Applied Biosystems", tools.invitrogen.com/content/sfs/manuals/cms.sub.- -039258.pdf, www.methods.info/Methods/DNA_methylation/Bisulphite_sequencing.html, each of which is expressly incorporated herein by reference. The method provides a noninvasive approach for detecting β-cell death in vivo that may be used to track the progression of diabetes and guide its treatment.

It is likewise understood that specific other tissues and cell types may have distinct methylation patterns from other tissues, and therefore that a corresponding technique, using appropriate PCR primers and optionally detection probes, may be used to detect apoptosis or other DNA release from these specific tissues or cell types into body fluids.

As an alternate to serum, saliva may also contain sufficient DNA containing epigenetic DNA modifications to provide a basis for diagnosis. During cell death most of the nuclear DNA is converted into nucleosomes and oligomers (Umansky, S. R., et al. [1982], "In vivo DNA degradation of thymocytes of gamma-irradiated or hydrocortisone-treated rats"; Biochim Biophys. Acta 655:9-17), which are finally digested by macrophages or neighboring cells. However, a portion of this degraded DNA escapes phagocytic metabolism, and can be found in the bloodstream (Lichtenstein, A. V., et al. [2001], "Circulating nucleic acids and apoptosis"; Ann NY Acad Sci, 945:239-249), and also in bodily fluids. The present invention addresses the detection of β-cell-specific epigenetic modifications that are detectable in bodily fluids such as plasma and saliva following the destruction of β-cells.

A method is provided for the sensitive and specific detection of β cell death in vivo in models of autoimmune and chemically induced diabetes in mice, in human tissues, and in serum from patients with T1D and T2D. This assay identifies a specific distinctive methylation pattern in the β cell DNA. This method provides a biomarker for detecting β cell loss in prediabetic mammals during progression of diabetes.

One embodiment of the method comprises the following steps:

1) Serum/plasma, or other body fluid is collected and DNA is extracted and substantially purified. Serum is reasonably available and usable, but collection of saliva or urine may be deemed less invasive.

2) Purified DNA is treated with bisulfite, whereupon the bisulfite converts demethylated cytosines to uracil while sparing the methylated cytosines (see en.wikipedia.org/wiki/Bisulfite_sequencing and "Methylation Analysis by Bisulfite Sequencing: Chemistry, Products and Protocols from Applied Biosystems", Invitrogen Corp. (2007) tools.invitrogen.com/content/sfs/manuals/cms_039258.pdf; see also en.wikipedia.org/wiki/DNA_methylation) (other methylation-sensitive distinctions may be exploited to distinguished between methylated and demethylated DNA, as known in the art).

3) Circulating DNA exists in relatively low abundance. Therefore, bisulfite treated DNA is subject to a first step polymerase chain reaction (PCR). This reaction is methylation insensitive and is designed to increase the availability of DNA template. PCR products are run on a standard gel electrophoresis and purified. Since the DNA is previously bisulfate treated, there will be distinct DNA subpopulations corresponding to methylated and demethylated Amylin gene DNA, for both the sense and antisense strands.

4) Purified DNA is used for a methylation sensitive reaction, that is, the reaction distinguishes between amplified DNA corresponding to methylated Amylin gene DNA and demethylated Amylin gene DNA (i.e., from β-cells). The reaction uses, for example, methylation sensitive probes to detect and differentiate demethylated Amylin DNA from β-cell origin from methylated Amylin DNA of non-β-cell origin.

Optionally, relative numbers of β-cell derived DNA are presented as "methylation index" or $2^{(methylated\ DNA - demethylated\ DNA)}$ or the difference between methylated DNA and demethylated DNA. Other quantitative analysis of the results, as well as historical trend analysis is possible. Further, the amount of β-cell derived DNA may be normalized on a different basis than non-β-cell derived DNA representing the Amylin gene. For example, a tracer similar in characteristics to the β-cell derived DNA (but unique with respect to endogenous DNA) may be quantitatively injected into a patient.

5) Provide a quantitative reference for the amount of β-cell derived DNA normalized for dilution, degradation, secretion/excretion factors, etc.

It is therefore an object to provide a method for monitoring β-cell pathology, comprising: extracting and purifying DNA from a body fluid of an animal; treating the extracted purified DNA with bisulfite to convert demethylated cytosine to uracil while sparing the methylated cytosines; amplifying the bisulfite-treated DNA using polymerase chain reaction; purifying the amplified bisulfite-treated DNA; performing a methylation sensitive reaction on the purified bisulfite-treated DNA using at least two different methylation specific probes which quantitatively distinguish between demethylated Amylin DNA of β-cell origin and methylated Amylin DNA of non-β-cell origin; and computing a quantitative relationship between methylated Amylin DNA and demethylated Amylin DNA.

It is a further object to provide a method for monitoring cell death of a cell type having at least one DNA portion that has a unique DNA CpG methylation pattern as compared to other cells, which is released into body fluids upon cell death of cells of the cell type, comprising: extracting and purifying DNA that comprises the DNA portion; treating the extracted purified DNA with bisulfite to convert cytosine to uracil while sparing the CpG methylated cytosines; amplifying a region of the bisulfite-treated DNA that comprises the DNA portion by polymerase chain reaction using DNA CpG methylation pattern independent primers; determining a quantitative relationship between the DNA portion having the unique DNA CpG methylation pattern to the DNA portion lacking the unique DNA CpG methylation pattern, by employing the DNA CpG methylation pattern-specific probes; computing a difference between the DNA portion having the unique DNA CpG methylation pattern and the DNA portion lacking the unique DNA CpG methylation pattern.

Another object provides a method for monitoring β-cell death, comprising: extracting and purifying genomic DNA from a body fluid of an animal, wherein the genomic DNA comprises at least a portion of a gene that is predominantly expressed by β-cells and that contains a CpG methylation site; treating the genomic DNA with bisulfite; performing a polymerase chain reaction (PCR) with primers that flank a region of the genomic DNA that comprises the CpG methylation site; purifying the PCR products; melting the PCR products into single strands; hybridizing the single-stranded PCR products with a first oligonucleotide probe capable of hybridizing with a target sequence that comprises a site corresponding to a bisulfite-converted CpG site and a second oligonucleotide probe capable of hybridizing with a target sequence that comprises a site corresponding to a bisulfite-nonconverted CpG site, and wherein the probes each comprise a non-FRET label pair consisting of a fluorophore and a quencher, and wherein interaction of the first oligonucleotide probe or second oligopeptide probe with a respective target causes the first oligopeptide probe or second oligopeptide probe to change from a first conformation to a second conformation, thereby changing the distance between the fluorophore and quencher of said label pair, and wherein in only one conformation do the fluorophore and quencher interact sufficiently to quench the fluorescence of the fluorophore by a predetermined amount; quantitatively measuring fluorescent signals emitted by the first oligopeptide probe and the second oligopeptide probe; and reporting a quantitative relationship of the fluorescent signal emitted by the first oligopeptide probe and the second oligopeptide probe, indicative of the relative amount of β-cell-derived DNA versus non-β-cell-derived DNA.

It is also an object to provide a kit for detecting β-cell-derived demethylated genomic DNA in a biological sample, wherein the kit comprises: PCR primers that flank a portion of a gene that is predominantly expressed by β-cells and contains a CpG methylation site; a first oligonucleotide probe capable of hybridizing with a first target sequence on a PCR product made using the PCR primers, wherein the first target sequence corresponds to at least one bisulfite-converted CpG site of the portion of the gene; and a second oligonucleotide probe capable of hybridizing with a target sequence on a PCR product made using the PCR primers of the kit, wherein the target sequence corresponds to at least one bisulfite-nonconverted CpG site of the portion of the gene, wherein the first oligonucleotide probe and the first oligopeptide probe each comprise label that allows selective quantitation of the first oligopeptide probe and the second oligopeptide probe. Each probe may comprise a label pair consisting of a fluorophore and a quencher, and wherein a binding interaction of the first oligopeptide probe with the first target sequence, and the second oligopeptide probe with the second target sequence, causes a change from a first conformation to a second conformation, thereby changing an interaction between the fluorophore and quencher of said label pair, and wherein in only one conformation of the first and second conformations do the labels interact sufficiently to quench the fluorescence of the fluorophore by, e.g., at least 25 percent, for example at least 50 percent.

The probes may be conjugated to a fluorophore and/or a quencher. The fluorophore may be at least one of 6-carboxy fluorescein and tetrachlorofluorescein. The quencher may be tetramethylrhodamine The probe may employ a fluorescent resonant energy transfer (FRET) interaction between the fluorophore and quencher, wherein the fluorophore and quencher are selectively separated in dependence on a binding of the probe to a respective target. The probe may also employ a non-FRET interaction between the fluorophore and quencher, wherein the fluorophore and quencher have an interaction based on a conformation of the probe, and in which the conformation is selectively dependent on a binding of the probe to a respective target.

The methylation sensitive reaction may comprises quantitatively determining a release of a fluorophore from a probe bound to the purified bisulfite-treated DNA.

The DNA portion having the unique DNA CpG methylation pattern may comprise an Amylin gene from a β-cell. The body fluid may be, for example, blood, blood plasma, blood serum, urine, saliva, or tears. In various embodiments, the present technology substantially isolates nucleic acids from a sample of body fluid, for example blood plasma, urine, saliva, cerebrospinal fluid, lymph fluid, synovial fluid, or tears, for example.

A kit may be provided with a solid carrier capable of adsorbing the nucleic acids containing in a sample of a body fluid, for example blood plasma, urine, or saliva. The kit may also contain other components for example, reagents, in concentrated or final dilution form, chromatographic materials for the separation of the nucleic acids, aqueous solutions (buffers, optionally also in concentrated form for final adjusting by the user) or chromatographic materials for desalting nucleic acids which have been eluted with sodium chloride.

The kit may also contain additional materials for purifying nucleic acids, for example, inorganic and/or organic carriers and optionally solutions, excipients and/or accessories. Such agents are known and are commercially available. For solid phase nucleic acid isolation methods, many solid supports have been used including membrane filters, magnetic beads, metal oxides, and latex particles. Widely used solid supports include silica-based particles (see, e.g., U.S. Pub. App. 2007/0043216; U.S. Pat. No. 5,234,809; U.S. Pat. No. 5,405,951; WO95/01359; WO95/02049; WO92/07863). Inorganic components of carriers may be, for example, porous or non-porous metal oxides or mixed metal oxides, e.g. aluminum oxide, titanium dioxide, iron oxide or zirconium dioxide, silica gels, materials based on glass, e.g. modified or unmodified glass particles or ground glass, quartz, zeolite or mixtures of one or more of the above-mentioned substances. On the other hand, the carrier may also contain organic ingredients which may be selected, for example, from latex particles optionally modified with functional groups, synthetic polymers such as polyethylene, polypropylene, polyvinylidene fluoride, particularly ultra-high molecular polyethylene or HD-polyethylene, or mixtures of one or more of the above-mentioned substances.

In addition, the reagent kit may also contain excipients such as, for example, a protease such as proteinase K, or enzymes and other agents for manipulating nucleic acids, e.g. at least one amplification primer, and enzymes suitable for amplifying nucleic acids, e.g. DNase, a nucleic acid polymerase and/or at least one restriction endonuclease. Alternately, a commercial polymerase chain reaction kit may be used to amplify the DNA samples, as discussed below. DNA is subject to degradation by DNases present in bodily fluids, such as saliva. Thus, in certain embodiments, it is advantageous to inhibit DNase activity to prevent or reduce the degradation of DNA so that sufficiently large sequences are available for detection.

After collection, the sample may be treated using one or more methods of inhibiting DNase activity, such as use of ethylenediaminetetraacetic acid (EDTA), guanidine-HCl, GITC (Guanidine isothiocyanate), N-lauroylsarcosine, Na-dodecylsulphate (SDS), high salt concentration and heat inactivation of DNase. After collection, the sample may be treated with an adsorbent that traps DNA, after which the adsorbent is removed from the sample, rinsed and treated to release the trapped DNA for detection and analysis. This not only isolates DNA from the sample, but, some adsorbents, such as Hybond™ N membranes (Amersham Pharmacia Biotech Ltd., Piscataway, N.J.) protect the DNA from degradation by DNase activity.

In some cases, the amount of DNA in a sample is limited. Therefore, for certain applications, sensitivity of detection may be increased by known methods. Where DNA is present in minute amounts, larger samples can be collected and thereafter concentrated such as by butanol concentration or concentration using Sephadex™ G-25 (Pharmacia Biotech, Inc., Piscataway N.J.).

Once obtained, the bodily fluid derived DNA may be used as an alternate to serum-derived DNA as discussed below. Since the technology is ratiometric, it is dependent not on the absolute quantity of DNA available, but the proportional relationships of the methylated and unmethylated portions. In general, the disposition of these types in the various body fluids is not believed to be highly dependent on the fluid type, and calibration techniques can be used to account for persistent and predictable differences in the fluid methylated/unmethylated ratios.

In various embodiments, the methylation status-specific probes are conjugated with 6-carboxyfluorescein, abbreviated as FAM, thus permitting quantitative detection. See, en.wikipedia.org/wiki/TaqMan. Other technologies may be used I conjunction with the present method; see, U.S. Pat. Nos. 6,103,476, 8,247,171, 8,211,644, 8,133,984, 8,093,003, 8,071,734, 7,972,786, 7,968,289, 7,892,741, 7,847,076, 7,842,811 7,803,528, 7,776,529, 7,662,550, 7,632,642, 7,619,059, 7,598,390, 7,422,852, 7,413,708, 7,399,591, 7,271,265, 7,241,596, 7,183,052, 7,153,654, 7,081,336, 7,070,933, 7,015,317, 7,005,265, 6,811,973, 6,680,377, 6,649,349, 6,548,254, 6,485,903, 6,485,901. Probes may be Fluorescent Resonance Energy Transfer (FRET) or non-FRET type. See, U.S. Pat. No. 6,150,097.

Various DNA extraction, isolation and purification technologies can be used, see, e.g., U.S. Pat. Nos. 4,935,342, 5,990,301, 6,020,124, 7,241,596, 6,485,903, 6,214,979, Re. 39,920.

An anion exchange material may be selected and employed which effectively adsorbs the target nucleic acids or protein complexes thereof. For example, commercially available anion exchange materials may be employed. Either strong or weak anion exchangers may be employed. A preferred weak exchanger can be one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers can be selected in relation to their respective absorption and elution ionic strengths and/or pH for the nucleic acid being separated. Purification by anion exchange chromatography is described in U.S. Pat. No. 5,057,426, EP 0,268,946 B1.

The material which is commercially available under the designation Q-Sepharose™ (GE Healthcare) is a particularly suitable. Q-Sepharose™, can be a strong anion exchanger based on a highly cross-linked, bead formed 6% agarose matrix, with a mean particle size of 90 µm. The Q-Sepharose™ can be stable in all commonly used aqueous buffers with the recommended pH of 2-12 and recommended working flow rate of 300-500 cm/h. In other preferred embodiments, the anion-exchange medium can be selected from sepharose-based quaternary ammonium anion exchange medium such as Q-filters or Q-resin.

The chromatographic support material for the anion charge used in the instant methods can be a modified porous inorganic material. As inorganic support materials, there may be used materials such as silica gel, diatomaceous earth, glass, aluminum oxides, titanium oxides, zirconium oxides, hydroxyapatite, and as organic support materials, such as dextran, agarose, acrylic amide, polystyrene resins, or copolymers of the monomeric building blocks of the polymers mentioned.

The nucleic acids can also be purified by anion exchange materials based on polystyrene/DVB, such as Poros™ 20 for medium pressure chromatography, Poros™ 50 HQ, of the firm of BioPerseptive, Cambridge, U.S.A., or over DEAE Sepharose™, DEAE Sephadex™ of the firm of Pharmacia, Sweden; DEAE Spherodex™, DEAE Spherosil™, of the firm of Biosepra, France.

A body fluid sample, such as blood plasma, saliva, or urine, containing nucleic acids or their proteinous complexes, is applied to the selected anion exchange material, and the nucleic acids or their complexes become adsorbed to the column material.

The contact and subsequent adsorption onto the resin can take place by simple mixing of the anion exchange media with the body fluid, with the optional addition of a solvent, buffer or other diluent, in a suitable sample container such as a glass or plastic tube, or vessel commonly used for handling biological specimens. This simple mixing referred to as batch processing, can be allowed to take place for a period of time sufficiently long enough to allow for binding of the nucleoprotein to the media, preferably 10 to 40 min. The media/complex can then be separated from the remainder of the sample/liquid by decanting, centrifugation, filtration or other mechanical means. The anion exchange material can optionally be washed with an aqueous solution of a salt at which the nucleic acids remain bound to the anion exchange material, the washing being of sufficient volume and ionic strength to wash the non-binding or weakly binding components through the anion-exchange material. In some embodiments, the resin can be washed with 2×SSC (300 mM NaCl/30 mM sodium citrate (pH 7.0). Preferred ranges of the salt solutions are 300-600 nM NaCl/30 mM sodium citrate (pH 7.0). The resin may alternately be washed with 300-600 mM LiCl/10 mM NaOAc (pH 5.2). The bound nucleic acids may then be eluted by passing an aqueous solution through the anion exchange material of increasing ionic strength to remove in succession proteins that are not bound or are weakly bound to the anion-exchange material and the nucleic acids of increasing molecular weight from the column. Both proteins and high and low molecular weight nucleic acids (as low as 10 base pairs) can be selectively eluted from the resin stepwise with the salt solution of concentrations from 300 mM to 2.0 M of NaCl and finally with 2.0 M guanidine isothiocyanate. LiCl solutions in the concentration range of 300 mM to 2.0 M of LiCl may also be used for stepwise elution.

The nucleic acids isolated may be in double-stranded or single-stranded form.

The body fluid can be pre-filtered through a membrane and supplemented with 10 mM EDTA (pH 8.0) and 10 mM Tris-HCL (pH 8.0) prior to adsorption onto the anion-exchange medium. Commercial sources for filtration devices include Pall-Filtron (Northborough, Mass.), Millipore (Bedford, Mass.), and Amicon (Danvers, Mass.). Filtration devices which may be used are, for example, a flat plate device, spiral wound cartridge, hollow fiber, tubular or single sheet device, open-channel device, etc. The surface area of the filtration membrane used can depend on the amount of nucleic acid to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

The body fluid, for example blood plasma, saliva or urine, can be supplemented with EDTA and Tris-HCL buffer (pH 8.0) and digested with proteinases, such as for example Proteinase K, prior to adsorption onto the anion exchange medium.

The anion-exchange medium can be immobilized on an individualized carrier such as a column, cartridge or portable filtering system which can be used for transport or storage of the medium/nucleoprotein bound complex. The nucleic acid/anion exchange may be maintained in storage for up to 3 weeks.

As used herein, "isolated" refers to a nucleic acid which is removed from cellular components and natural body fluids.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A: Sanger sequencing of bisulfite treated DNA from various tissues. Red arrows point to a mixed signal consisting of cytosine (C) and thymidine (T) in DNA from whole pancreas and purified mouse islets, indicating a mixed population of methylated CpG dinucleotides. FIG. 2B: Schematic depiction of differentially methylated CpG dinucleotides in the mouse amylin coding region used for the design of methylation-specific primers. FIG. 2C: Methylation-specific primers were tested over a wide range of $10^6$ dilution factors for assay sensitivity and specificity using artificially synthesized methylated and demethylated DNA sequences. Demethylation index was calculated as (DMI)=$2^{(methylated\ cycle\ number)-(demethylated\ cycle\ number)}$ ($R^2=0.9863$, $p<0.0001$). FIG. 2D: qRTPCR reaction using methylation-sensitive primers on bisulfite treated DNA from liver, stomach, pancreas and islets and immortalized murine cell lines MS1 (islet endothelium–negative control) and βTC3 (insulinoma–positive control). Data consists of three independent analyses. Assay reproducibility as measured by CV=11.32±2.62.

FIGS. 3A-3G show that Demethylated amylin DNA is increased in the blood of pre-diabetic NOD mice during T1D progression. 8 wk old female NOD mice were housed in SPF conditions and monitored for 12 weeks for the development of diabetes. Blood from each animal was collected on wk 8, 14, 18 and 20. FIG. 3A: IPGTT values of pre-diabetic NOD mice at various ages over 120 minutes. FIG. 3B: Immunofluorescence staining of representative islets from NOD mice at various ages. Blue-DAPI. Green-Amylin. Red-Insulin. White-GLUT2. Note the appearance of insulin⁻ amylin⁺GLUT2⁺ β-cells in islets from diabetic NOD mice. FIG. 3C: Aggregate DMI and glucose values in NOD mice collected over 12 weeks (n=14). FIGS. 3D-3G: Representative data from four individual NOD mice. DNA concentration in the serum was measured using picogreen. DMI was calculated on bisulfite treated serum-derived DNA. Variability in disease onset and β-cell DNA is characteristic of the spontaneous nature of T1D in the NOD mouse model.

FIG. 4A: Schematic depiction of differentially methylated CpG dinucleotides in the human amylin coding region used for the design of methylation-specific primers. FIG. 4B: Human methylated specific primers were tested over a wide range of $10^6$ dilution factors for assay sensitivity and specificity using artificially synthesized methylated and demethylated DNA sequences. ($R^2=0.9955$, $p<0.0001$). FIG. 4C: qRTPCR reaction using methylation-sensitive primers on bisulfite treated DNA from liver, purified human islets and magnetic beads enriched human β-cells. FIG. 4D-Demethylation index for liver, islets and β-cells. Data from liver and human islets consists of two independent repeats.

FIG. 5A: DMI values for healthy control (HC, closed circles) and recent onset T1D patients (RO, closed squares). $p<0.015$. FIG. 5B: ROC analysis of patient data. AUC=0.866, with 95% confidence interval 0.72 to 1.01, $p<0.0018$. FIG. 5C: Correlation analysis between HbA1c and DMI values in RO patients. FIG. 5D: Data presentation of insulin/amylin DMI per RO patient. Pearson's r=0.63, $p<0.028$.

DETAILED DESCRIPTION OF THE PREFERRED EMBODIMENTS

Figure 1:
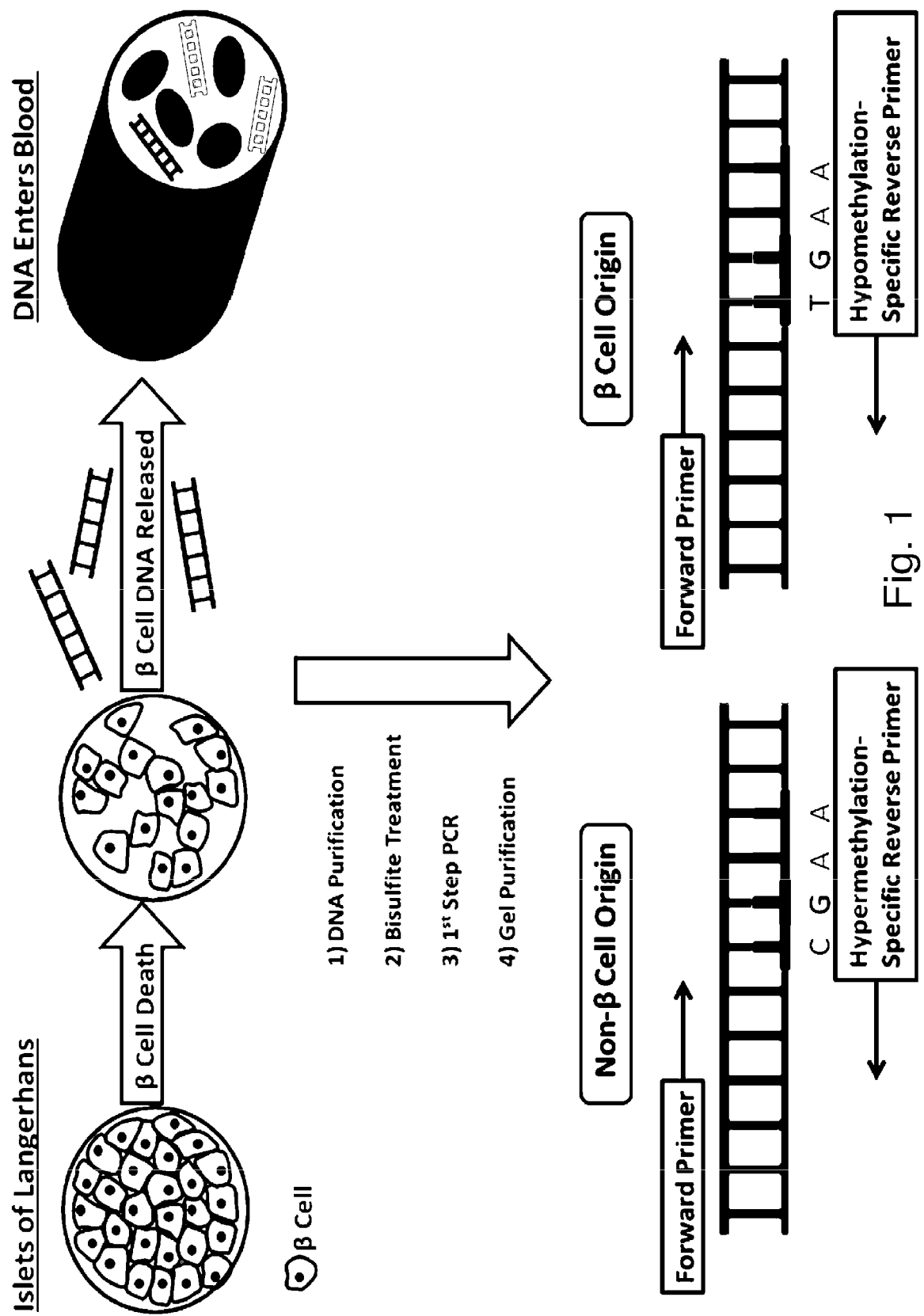
FIG. 1 shows a schematic depiction of amylin-based biomarker assay for the detection of β-cell loss in T1D. β-cells within the islets of Langerhans die, releasing genomic DNA into circulation. Blood samples are taken from subject and DNA purified and subjected bisulfite conversion. Bisulfite converted DNA is subjected to 1st step PCR reaction using methylation unspecific primers, and run on agarose gel. 1st step PCR product is purified from agarose gel and used as template for qRTPCR using methylation-specific primers.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Experimental

Female NOD/LtJ mice were obtained pathogen-free from the Jackson Laboratory (Bar Harbor, Me.) and maintained under pathogen-free conditions. Eight-wk old NOD mice were screened for hyperglycemia every 2-4 wks and were diagnosed with diabetes when glucose levels >200 mg/dL were measured in whole blood from the tail vein using a Glucometer Elite XL (Bayer A.G., Whippany, N.J.). Blood for DMI analysis was collected by cheek pouch bleeding, thereby allow for monitoring of β-cell death in the same animal until the development of frank hyperglycemia. All animal use and husbandry protocols were approved by the Winthrop-University Hospital Institutional Animal Care and Use Committee.

Intraperitoneal glucose tolerance test (IPGTT) was done as previously described (Akirav (Diabetes 2011)). In brief, mice undergoing an IPGTT were fasted overnight and received a 2 g/kg intraperitoneal (i.p.) dextrose injection. Whole-blood glucose levels were measured from the tail vein at 0 15, 30, 60, and 120 min after injection.

Immunofluorescence was done as described in Akirav (Diabetes 2011). Pancreata were resected and fixed for 24 h in 2% PFA. After fixation, pancreatic tissues were placed in a sucrose gradient and snap frozen in liquid nitrogen. Noncontiguous 14-mm pancreatic sections were stained with antibodies to insulin (Abcam, Cambridge, Mass.), amylin (Abcam, Cambridge, Mass.), and glucose transporter 2 (GLUT2, Santa Cruz, Santa Cruz, Calif.). The bound antibodies were detected by immunofluorescent secondary antibodies (Jackson Immunoresearch, West Grove, Pa.). Nuclear staining was done using 4',6-diamidino-2-phenylindole dihydrochloride (DAPI), The slides were analyzed by fluorescence microscopy using a Nikon Eclipse Ti confocal microscope (Nikon, Melville, N.Y.).

MS1 mouse pancreatic islet endothelial cells (American Type Culture Collection, Manassas, Va., catalog number CRL-2279) were cultured and stored using provided protocols. Mouse βTC3 insulinoma cells were a gift from Albert Einstein College of Medicine (Bronx, N.Y.), and culture protocols are previously described in Spelios (2015), Spelios (2013). Human EndoC-βH1 cells were obtained from Dr. R. Scharfmann laboratory, (CRICM, Paris, France) and were cultured as described in Ravassard (2011). Human Islet samples were received from the Integrated Islet Distribution Program (IIDP, Duarte, Calif.) (donor numbers 971, 1265 and 1393).

Human Primary β-cells were isolated by magnetic bead purification using the AutoMACS cell sorter (Miltenyi Biotech Inc., San Diego, Calif.) as described by Banerjee (2009). In brief, human islets were washed once, subjected to trypsin disassociation, and filtered using a 70 μm nylon mesh. Dispersed islets were stained using anti-human CA19-9 antibodies (Miltenyi Biotech Inc., San Diego, Calif.) and ran through the AutoMACS. The negative fraction was stained using PSA-NCAM microbeads (Miltenyi Biotech Inc., San Diego, Calif.) and the positive fraction was sorted using the AutoMACS. CA19-9$^-$PSA-NCAM$^+$ cells were enriched for β-cells and were used for further analysis. Fraction enrichment was verified by measuring the signal of demethylated insulin DNA as described in Akirav (PNAS 2011).

Recent onset (RO) T1D and unrelated healthy control (HC) subjects were recruited through Children's Hospital of Wisconsin (CHW). RO T1D subjects (n=15) met diagnostic criteria of T1D as defined per World Health Organization criteria (Alberti 1998) and were positive for >1 AA. Samples were collected 2-7 months after clinical onset from subjects with histories of good glycemic control. HC (n=11) were free of known infection at sample collection and did not possess a family history of T1D. Details of the studied subjects are provided in Table 1. The study was approved by the Institutional Review Board of CHW (IRB 01-15) and written informed consent was obtained from subjects or their parents/legal guardians.

DNA was purified from sera, pelleted cells, and homogenized tissue using the DNEasy Blood and Tissue Kit (Qiagen N.V., Valencia, Calif.). The concentration of the purified DNA was measured using the Quant-iT PicoGreen dsDNA Assay Kit (Life Technologies, Carlsbad, Calif.). Purified DNA was bisulfite treated using the EZ DNA Methylation-Direct Kit (Zymo Research, Irvine, Calif.).

Prior to qPCR analysis, a non-methylation-specific PCR was run in order to increase DNA template. Sequences for the human and murine primers can be found in Tables 2 and 3. Bisulfite treated DNA was used as template for the reaction which was run using the EpiTaq HS Kit (Clonetech Laboratories Inc., Mountain View, Calif.). PCR products were run on a 2% agarose gel and purified using the QIAquick Gel Extraction Kit (Qiagen N.V., Valencia, Calif.). No template controls were used to exclude DNA contamination and showed no observable products in the first-step PCR reaction.

Gel purified human and murine islet DNA samples previously bisulfite treated and run on first-step PCR were used in a TOPO TA Cloning reaction and ligated to pCR 2.1TOPO vector (Invitrogen, Carlsbad, Calif.). Competent NEB 5-alpha E. coli (New England Biolabs, Ipswich, Mass.) were transformed with the TOPO ligation products, plated on ImMedia Kan Agar (Invitrogen, Carlsbad, Calif.), and incubated at 37° C. overnight. Colonies from both human and mouse samples were isolated, added to LB broth/Kanamycin culture, and shaken overnight at 37° C. TOPO plasmid DNA was purified from the cultures using the QIAprep Spin Miniprep Kit (Qiagen N.V., Valencia, Calif.). Purified plasmid DNA and gel extracted first-step PCR products were sequenced at the Keck Biotechnology Research Laboratory (New Haven, Conn.).

Purified DNA from human liver and beta cell fraction was treated with the McrBC methylation-specific restriction enzyme (New England Biolabs Inc., Ipswich, Mass.). After treatment, 0.8 ng of treated and untreated liver and beta cell fraction DNA, as well as a TOPO plasmid containing the appropriate native amylin insert (625,000 copies per reaction), were run on PCR using native amylin primers (Table 3). Samples run on PCR were removed at cycle 27 or 30.

PCR products were run on a 2% agarose gel and imaged using a 4000R Image Station (Eastman Kodak Co., Rochester, N.Y.).

Gel-purified first-step PCR products were used as template for qPCR using primers designed for bisulfite-converted demethylated and methylated amylin DNA. Both murine and human reactions were run using SsoAdvanced Universal SYBR Green Supermix (Bio-Rad Laboratories Inc., Hercules, Calif.). Primers and PCR protocols are reported in Tables 2 and 3. All reactions were run on a CFX96 Real Time System (Bio-Rad Laboratories Inc., Hercules, Calif.). Relative quantification of demethylated DNA was calculated by $DMI= 2^{(methylated\ cycle\ number)-(demethylated\ cycle\ number)}$.

Results are presented as mean±SEM. Statistical significance (p<0.05) of differences between means was determined by one-way ANOVA with Tukey's post hoc test using Prism 5 (GraphPad software).

Table 5 shows the primers and probes used to analyze the presence of demethylated insulin DNA, per Akirav US 20150376706.

Analysis

Figure 2A:
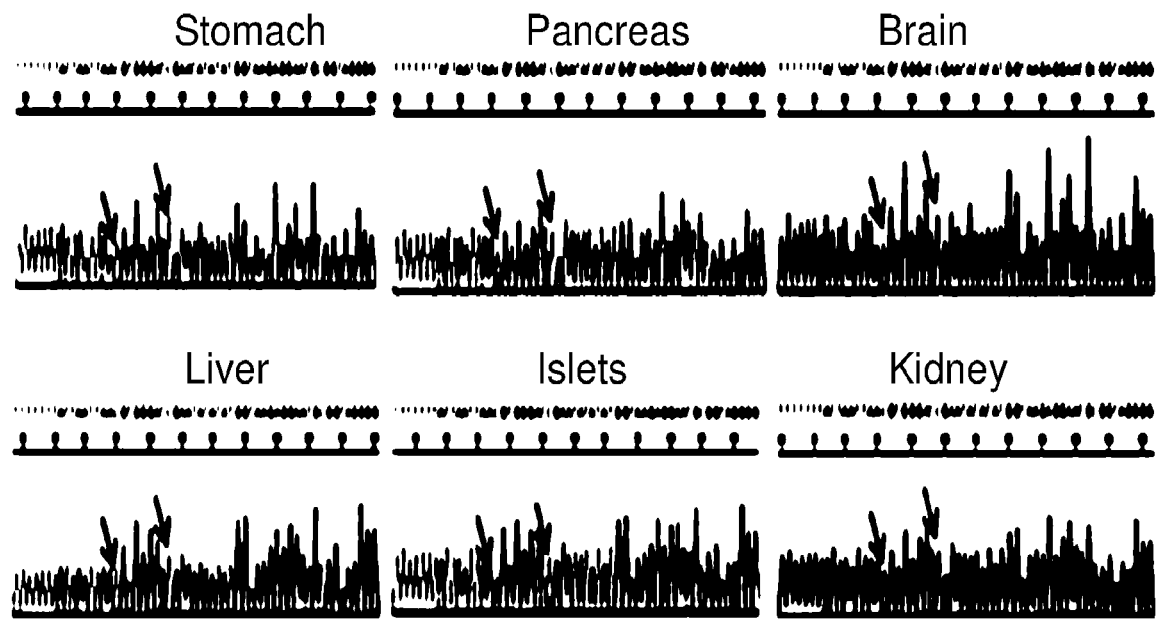
FIGS. 2A-2D show that Amylin DNA is demethylated in murine pancreas, islets and β-cells and can be selectively detected using demethylation specific primers.
Figure 2B:
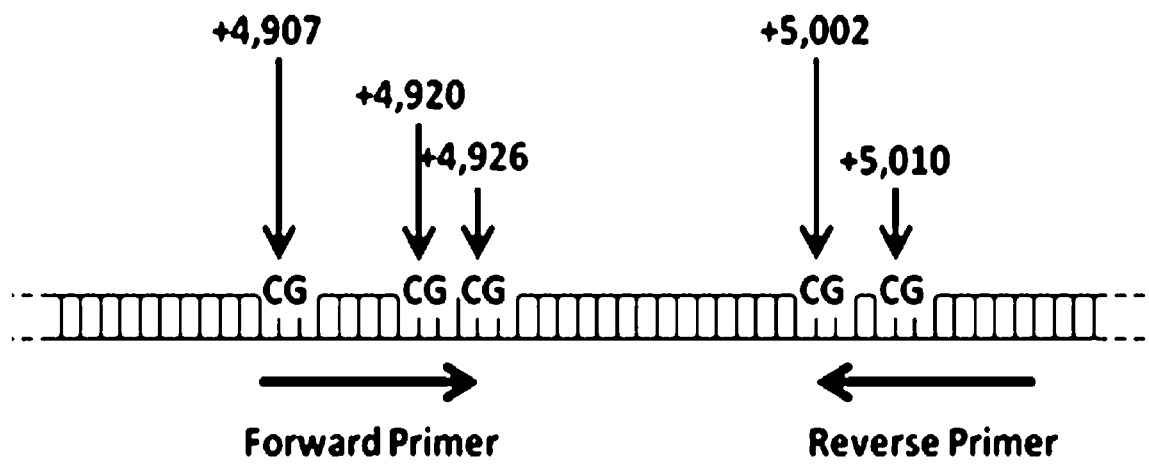
Figure 2C:
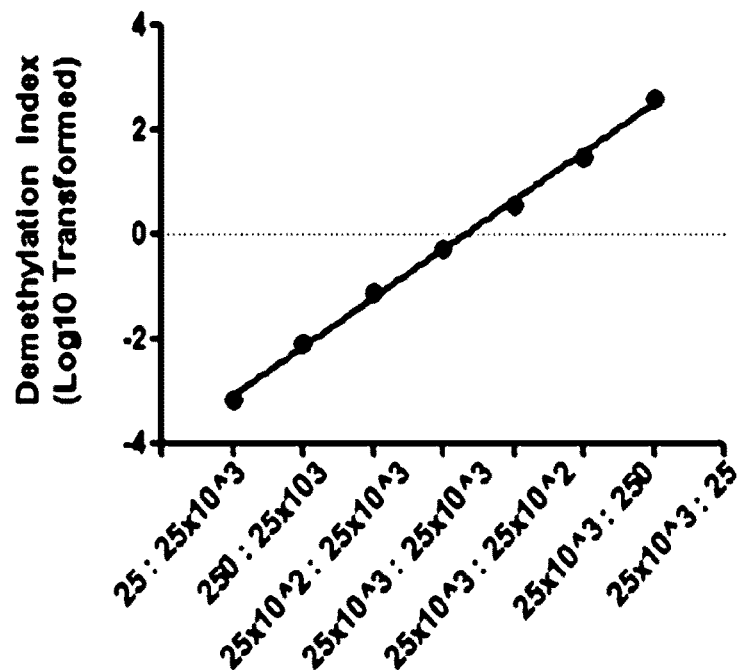
Figure 2D:
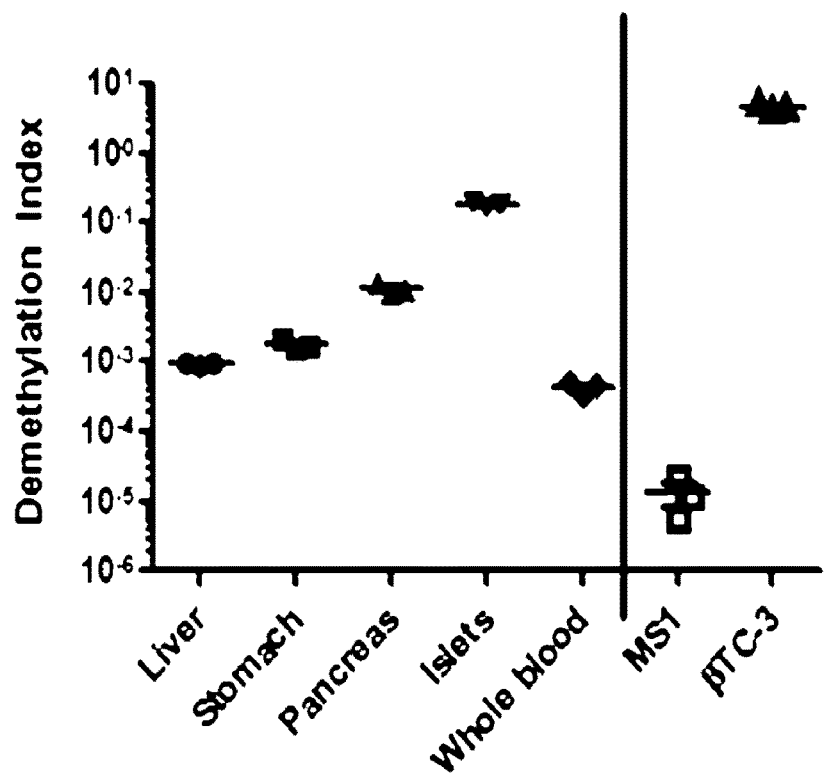

The reduced DNA methylation in both pancreas and primary islets prompted examination of whether methylation-specific primers are capable of differentiating methylated (Meth) from demethylated (DeMeth) amylin DNA. Five differentially methylated CpGs were chosen to be included in the forward and reverse primer sequences (FIG. 2B and Table 3). Synthetic DNA representing Meth or DeMeth amylin sequences were synthesized, cloned and sequence validated. These plasmids were then used to define primer sensitivity and specificity to their respective templates. Plasmids were mixed at variable copy numbers of 25, 250, 25×10$^2$ and 25×10$^3$ copies representing a range of 12.5 to 12,500 β-cells, respectively, over a six logarithmic concentration range and used to determine the specificity and sensitivity of methylation-specific primers. The relative abundance of the DeMeth DNA (representative of β-cell DNA) was expressed by using DMI as described in the materials and methods. FIG. 2C shows a strong linear correlation between increasing DeMeth DNA concentrations and DMI values (R2=0.9981, p<0.0001), demonstrating the ability of DeMeth specific primers to detect DeMeth DNA over a wide range of copies. Finally, methylation-specific primers were investigated for detection of β-cell DNA in primary tissues and murine cell lines. DMI values for purified mouse islets were ~190 fold higher than those measured in liver, indicating a high level of specificity of the DeMeth primers (FIG. 2D). Since DMI values are determined in cell-free serum, we examined the DMI levels of amylin in whole blood preparations from healthy mice. DMI values from whole blood showed low DMI levels similar to those detected in the liver and were significantly lower than the levels detected in purified islets (FIG. 2D). Comparison of DMI values between the murine insulinoma line, βTC3, and the islet-derived endothelial cell-line MS1 showed a ~106 increase in the former (FIG. 2D). Taken together, these data identify previously unreported demethylated CpG dinucleotides in the coding region of the amylin gene in primary islets and in βTC3 insulinomas. Primers designed to differentiate between Meth and DeMeth amylin DNA show a high degree of specificity and sensitivity when used to detect DeMeth and Meth DNA in primary murine islets and βTC3 cells. Assay coefficient of variation for DMI of all samples excluding MS1 (which showed very low hypomethylated DNA) was calculated at 11.32±2.68%.

The presence of differentially methylated CpG dinucleotides was identified in the coding region of the amylin gene in murine and human islets and β-cells. These unique patterns can be used as a biomarker of β-cell loss in the NOD mouse model of T1D and in patients with RO T1D. Since amylin protein expression persists in murine islets even after insulin expression has been lost, this assay can serve as a biomarker of β-cell loss in addition to the previously described insulin biomarker, Akirav (2011), thereby providing a dual-gene approach for evaluating β-cell loss in T1D.

The utility of differentially methylated insulin DNA as a biomarker of β-cell loss in T1D has been previously proposed, as insulin is uniquely expressed in these cells. Similarly, amylin is highly expressed in the islet by β-cells and secreted together with insulin. Analysis of methylation in the amylin gene coding region has revealed several unique demethylated patterns in β-cells when compared with other murine and human tissues. Similar methylation patterns were also found in insulinoma cells, suggesting that DNA methylation may play a role in the control of amylin expression in β-cells.

The presence of β-cell-specific methylation patterns in the amylin gene permitted development of methylation-specific primers capable of distinguishing between β-cell-derived DeMeth DNA and Meth DNA from all other tissues. Meth and DeMeth amylin DNA-sensitive primers for both murine and human amylin sequence showed a high degree of specificity and sensitivity when tested using cloned Meth and DeMeth amylin DNA. This was evident by the ability of the assay to maintain a linear pattern throughout a wide range of DNA concentrations, and an ability to detect as little as 25 copies of DeMeth DNA (equivalent to 12.5 β-cells) even when diluted in 25,000 copies of Meth DNA (equivalent to 12,500 non-β-cells). Analysis of DNA from different tissues showed similar results, with human and mouse islets and enriched β-cells yielding higher DMI values when compared with other tissues.

Methylation-specific primers provided a tool for detecting DeMeth DNA in serum of NOD mice. The loss of β-cells in this model has been extensively studied, and data showing a deterioration of both glucose tolerance and insulin staining in the islet support these findings. Immunofluorescence staining of islets from prediabetic and diabetic mice revealed a disconnect between insulin and amylin protein expression and were supported by an increase in amylin mRNA expression in human insulinomas following exposure to high dose streptozotocin. These findings in the islet are supported by a previous report demonstrating similar levels of amylin protein in the blood of prediabetic and diabetic NOD mice. The loss of insulin but not amylin expression in this subset of β-cells may make these cells invisible to a biomarker assay that relies solely on the detection of insulin cfDNA. Indeed, DeMeth amylin DNA levels were increased in prediabetic NOD mice reaching a peak at disease presentation, and were not correlated with DeMeth insulin levels in the serum. Sufficient cfDNA for an analysis is available by periodic cheek pouch bleeding in the same mouse, permitted by the sensitivity of the assay. This approach allows for a longitudinal view of diabetes progression and a measure of β-cell loss over time.

The human amylin coding region shares a high degree of sequence homology with the mouse gene. Homologous sequences in human amylin DNA demonstrated differential methylation between β-cells and liver by methylation-sensitive enzymatic DNA digestion. Methylation-specific amylin primers showed a high degree of specificity and sensitivity to artificially DeMeth DNA as well as DNA from primary human islets and enriched β-cells. When used to test the levels of DeMeth amylin DNA in human subjects, these primers demonstrated a statistically significant increase in DeMeth amylin cfDNA in RO T1D patients when compared with unrelated HC, with good assay specificity and sensitivity by ROC analysis. Moreover, the mild correlation between DMI and HbA1c values may suggest that diabetes severity due to poor metabolic control and immune dysregulation may contribute to β-cell loss. Finally, although DMI values of amylin and insulin cfDNA were in overall agreement in RO T1D patients, amylin cfDNA levels showed a stronger increase in amylin signal than insulin, suggesting that amylin expression may persist in the islets of diabetic patients in a similar fashion to diabetic NOD mice. This is supported by prior reports showing a deviation in the concentration of c-peptide/insulin and amylin in the plasma of T1D patients. An alternative explanation may relate to the fact that the levels of cfDNA in the blood are low, thereby allowing for the detection of amylin but not insulin in some serum samples and vice versa. In any event, the combination of both insulin and amylin DMI offers a unique opportunity for a dual gene approach to measure β-cell loss, which would otherwise remain undetected by the insulin biomarker assay. This dual gene assay enhances assay validity and reliability by expanding assay measurement to more than a single gene for β-cell loss detection.

Differential methylation of the amylin gene is found in the islet and in enriched β-cells. This differential methylation of amylin in β-cells provides an opportunity to detect the presence of β-cell-derived DeMeth amylin cfDNA by using methylation-specific primers. The identification of amylin⁺ insulin⁻ β-cells highlights the importance of using amylin cfDNA as an additional biomarker of β-cell death in RO T1D patients in conjunction with our previously reported insulin gene.

Figure 3A:
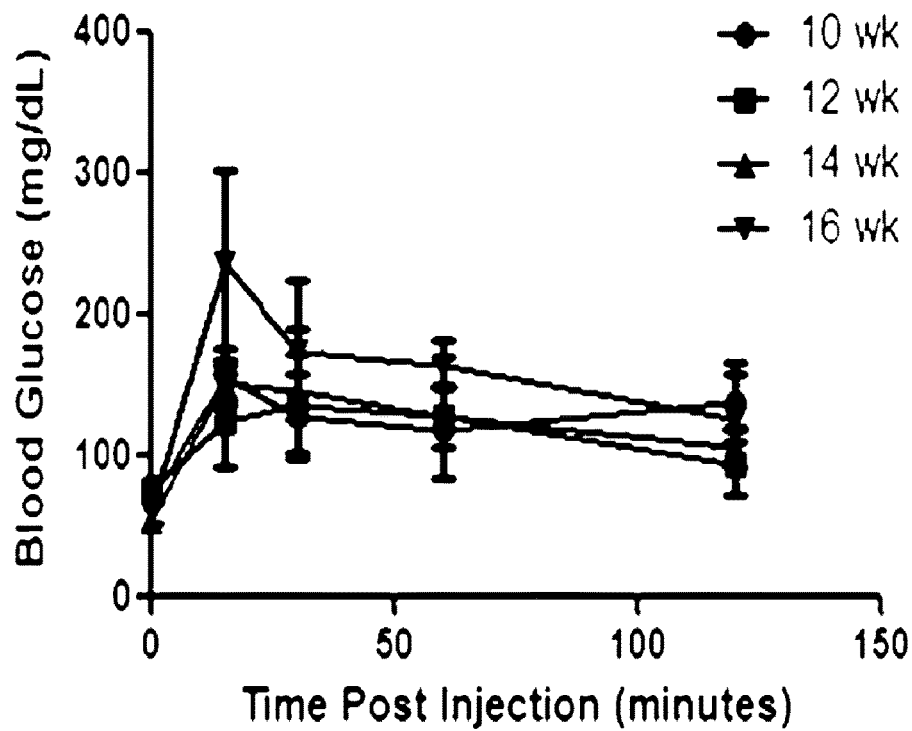
Figure 3B:
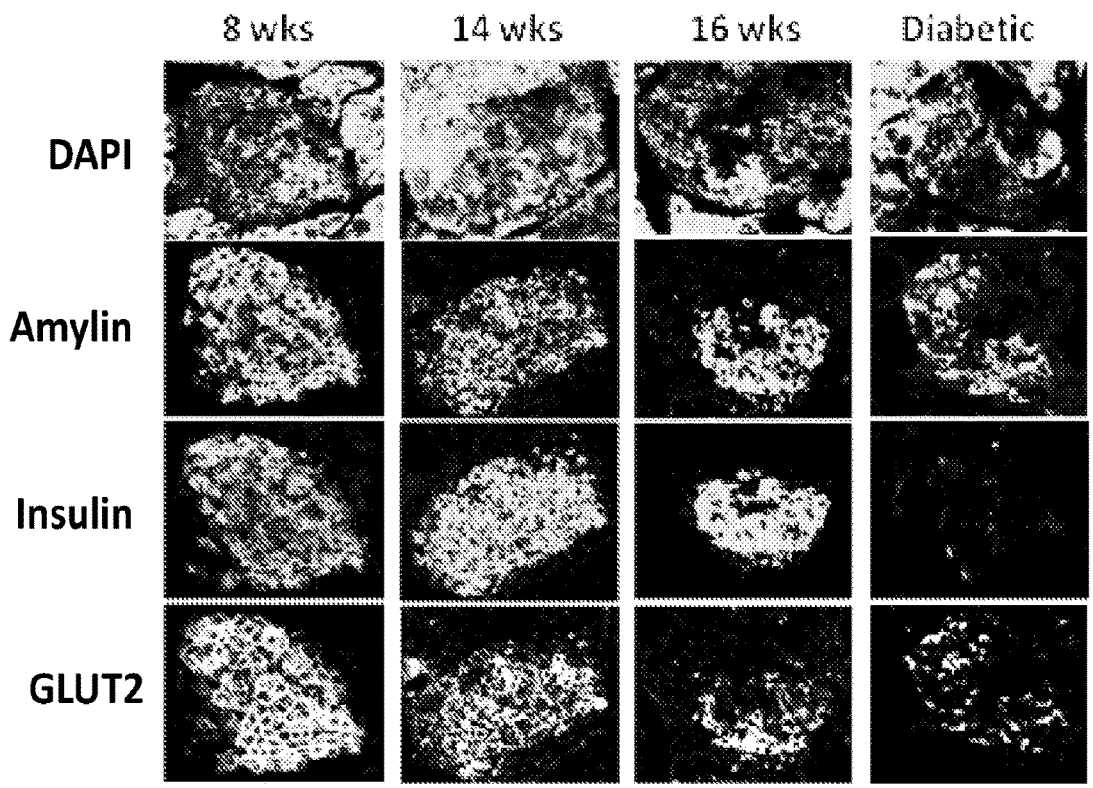
Figure 3C:
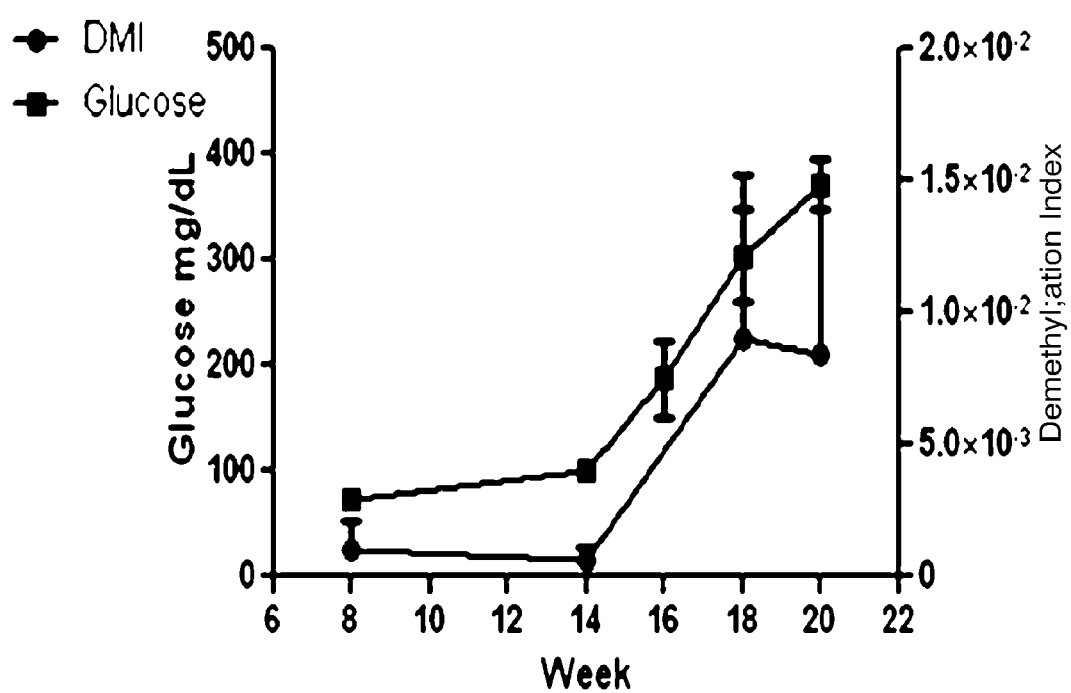

Amylin expression in the islet and demethylated amylin cfDNA are detected at the time of T1D in NOD mice. DeMeth insulin cfDNA levels are increased during the natural progression of T1D in the NOD mouse and are reduced following the development of hyperglycemia, demonstrating the utility of DeMeth insulin DNA as a biomarker of insulin-expressing β-cell death in prediabetes. 8 wk to 20 wk old NOD mice were followed for the development of hyperglycemia. Cheek pouch bleeding was used for blood collection, thereby providing a longitudinal view of β-cell death in the same animal. IPGTT analysis showed a gradual deterioration in glucose tolerance at 16 wks of age (FIG. 3A). IF analysis of insulin and amylin expression showed marked reduction in insulin expression at 16 wks. However, amylin expression remained relatively stable and amylin+/insulin− islets were observed throughout the pancreas well after diabetes was established (FIG. 3B). These cells stained positive for GLUT2 confirming their β-cell phenotype (FIG. 3B). This surprising finding suggests that a subset of amylin-expressing β-cells may persist following the development of hyperglycemia, which may otherwise remain undetected by insulin staining. Analysis of DMI values in NOD mice of different age showed an increase in β-cell death during diabetes progression (FIG. 3C), with DeMeth amylin cfDNA peaking at the time of disease presentation. Analysis of insulin and amylin DMIs in individual NOD mice revealed a high degree of variability in DMI values prior to or during the presentation of hyperglycemia (FIGS. 3D-3G). All in all, insulin and amylin DMI levels were discordant during the period of prediabetes but tended to follow a similar pattern at the time of diabetes presentation, suggesting that the two biomarkers may present two independent measurements of different β-cell subsets in these mice. Taken together, these results identify a β-cell population which remains amylin positive while losing insulin expression and demonstrate the ability of methylation-specific primers to detect an increase in amylin cfDNA at the time of disease presentation in the NOD model of T1D.

Figure 4A:
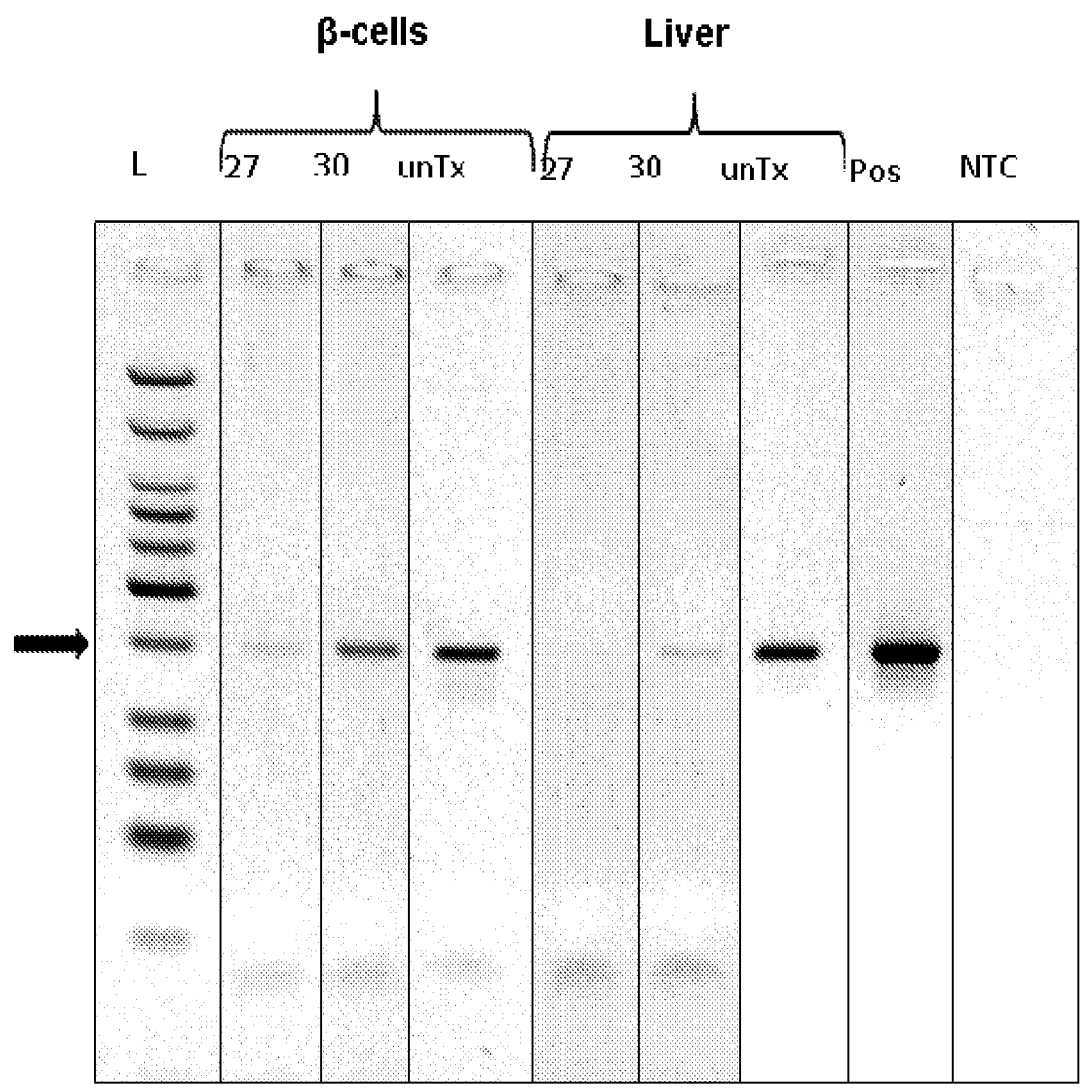
FIGS. 4A-4D show methylation-specific primers show a high degree of specificity and sensitivity and detect demethylated DNA in primary human islets and enriched human β-cells.
Figure 4B:
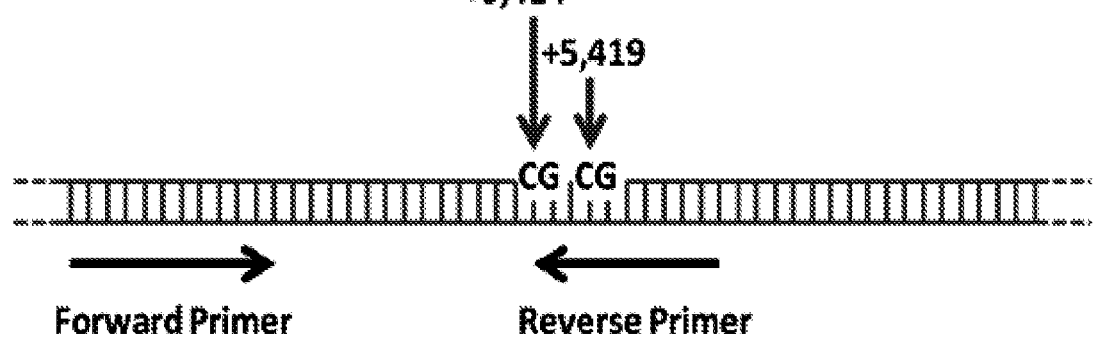
Figure 4C:
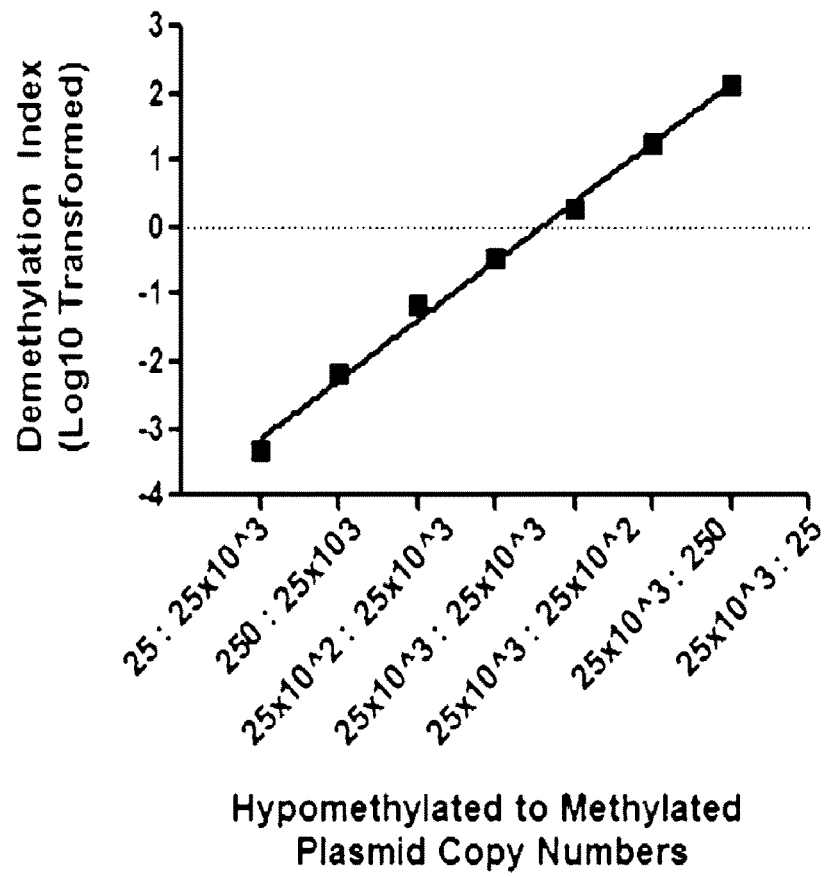

Amylin DNA is demethylated in both primary human islets and enriched human β-cells and can be detected by methylation-specific primers. The region used for the construction of methylation-specific amylin primers in the mouse is conserved in the human amylin gene. Analysis of DNA methylation by the methylation-sensitive restriction enzyme, McrBC, revealed the presence of demethylated amylin DNA in magnetic bead-enriched β-cell fractions when compared with liver fractions (FIG. 4A). The presence of differentially methylated CpGs in the human amylin gene allowed for the design of methylation-specific primers (FIG. 4B and Table 4). Plasmid containing synthetic DNA representing human Meth or DeMeth amylin sequences were cloned and validated by sequencing, mixed at variable copy numbers of 25, 250, $25 \times 10^2$ and $25 \times 10^3$ copies over a six logarithmic concentration range, and analyzed by qPCR. qPCR analysis of DeMeth amylin showed a high degree of positive correlation between PCR signal and the number of DeMeth amylin DNA even when diluted at 1:1000 ratio in Meth amylin DNA (FIG. 4C, $R^2=0.9930$, $p<0.0001$).

Figure 4D:
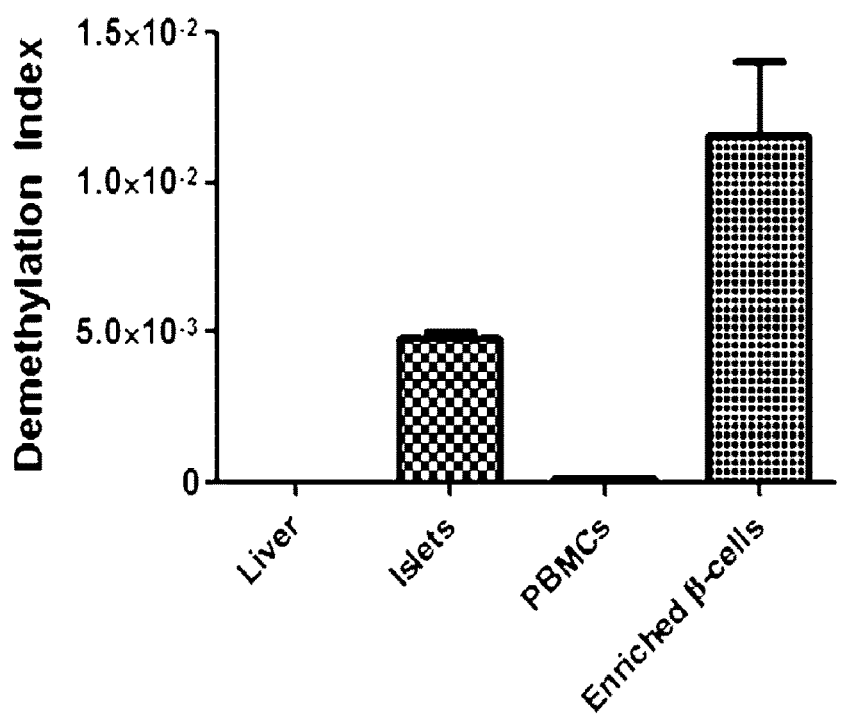

To determine whether methylation-specific primers were capable of detecting DeMeth β-cell DNA, DNA from liver, islet and magnetically-enriched β-cells was isolated and analyzed by qPCR. DeMeth amylin DNA specific primers detect increased DMI values in primary human islets and enriched human β-cells. The region used for the construction of methylation-specific amylin primers in the mouse is conserved in the human amylin gene (FIG. 4A), Primers specific for the Meth and DeMeth human amylin gene (Table 4) were developed. These were tested with synthetic DNA representing human Meth or DeMeth amylin sequences that were cloned using the TOPO-cloning system. Sequence validated plasmids were mixed at variable ratios over six logarithmic concentrations and qRTPCR was conducted using methylation-specific primers. qRTPCR analysis for DeMeth amylin showed a high degree of positive correlation in the presence of Meth amylin, suggesting a high degree of assay specificity for DeMeth β-cell derived DNA (FIG. 4B, $R^2=0.9955$, $p<0.0001$). To determine whether methylation-specific primers were capable of detecting β-cells, DNA from liver, islet and magnetic beads enriched β-cells was isolated, bisulfite converted, subjected to a $1^{st}$ step PCR, gel purified, and analyzed by qRTPCR. DMI values of primary human islets were ~590 fold higher than liver, while enriched β-cells were ~1,440 fold higher than liver (FIG. 4D). This increase was consistent with amylin mRNA expression in β-cells (data not shown). Similarly to mouse, DMI values of DNA from peripheral blood mononuclear cells (PBMCs) were considerably lower than enriched β-cells (FIG. 4D). Amylin gene methylation stability was tested by exposing the EndoC-βH1 human insulinoma cells to streptozotocin (STZ) for 24 and 48 hrs, showing steady DMI values between untreated and STZ-treated cells. Taken together, methylation-specific primers for genomic amylin DNA show good assay sensitivity/specificity when tested using artificial DNA and primary human tissues. The overall increase in DMI in primary human islets and enriched β-cells suggests that methylation-specific primers may be used to detect β-cell-derived DeMeth amylin DNA in peripheral blood samples.

DeMeth amylin cfDNA is increased in plasma of recent onset T1D patients. Amylin cfDNA levels were increased at the time of disease onset and persisted in diabetic NOD mice, and this technique may be adapted to detect the human amylin gene. Methylation-specific human amylin primers were tested for detection of amylin cfDNA in plasma samples from RO T1D patients and age-matched unrelated HC collected at the Children's Hospital of Wisconsin. Plasma samples were processed and cfDNA extracted, bisulfite-converted, and subjected to first step PCR. Amplicons were gel-purified to remove impurities and qPCR was done using methylation-specific primers.

Figure 5A:
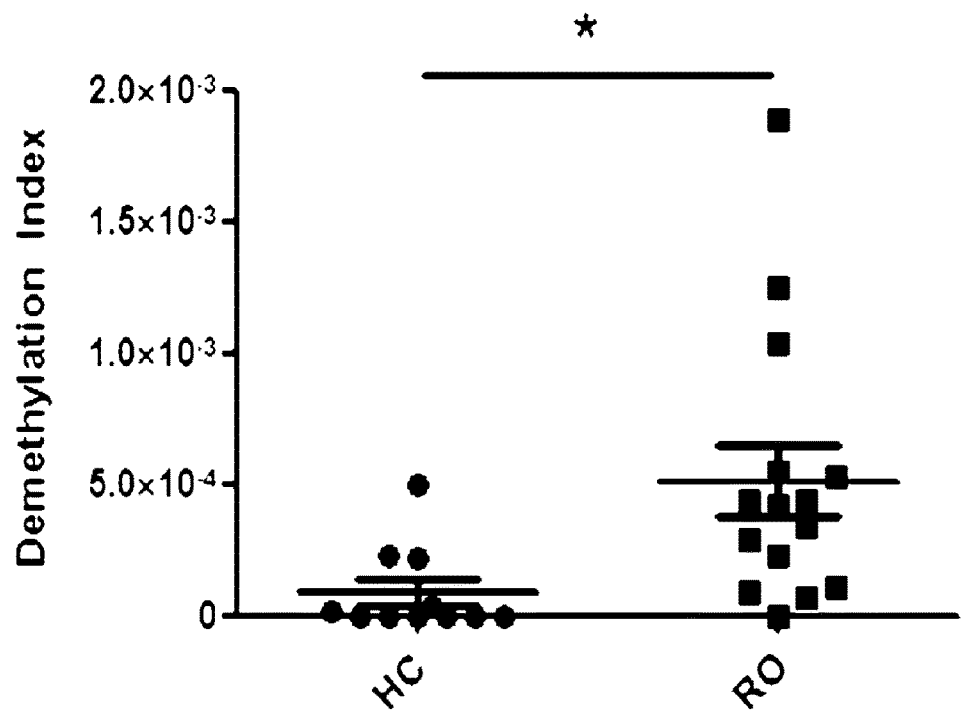
FIGS. 5A-5D show methylation specific primers show increased demethylated amylin DNA in the blood of patients with recent onset T1D.
Figure 5B:
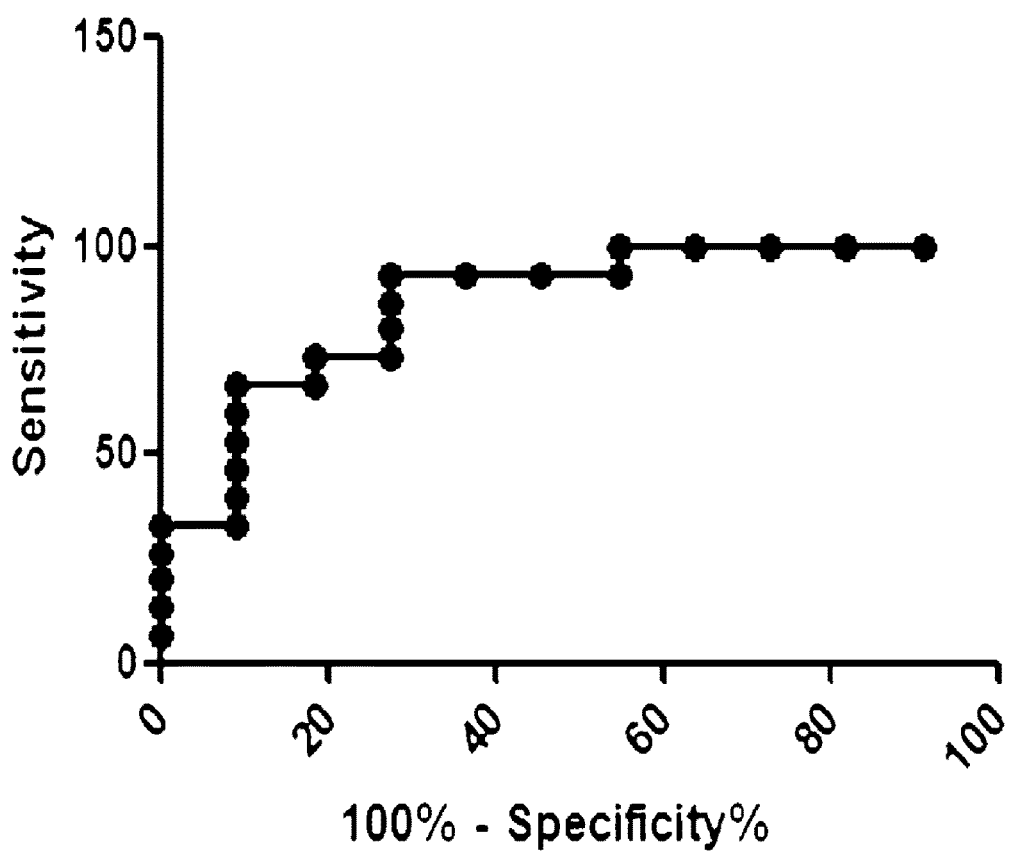
Figure 5C:
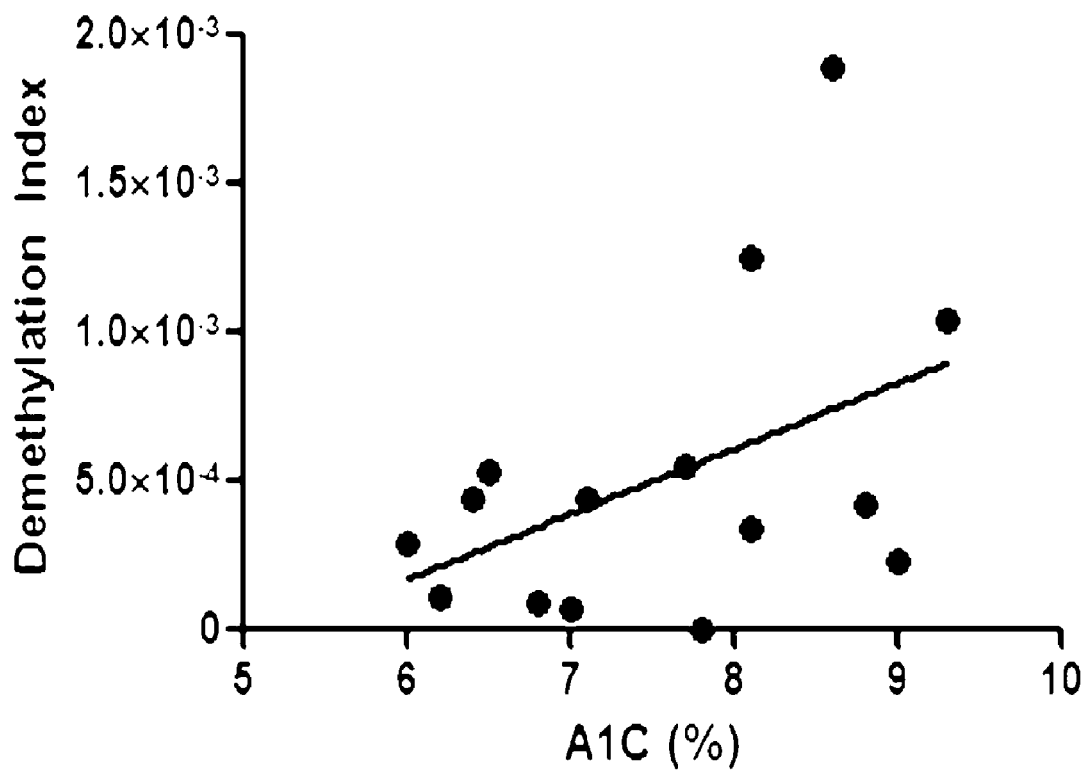
Figure 5D:
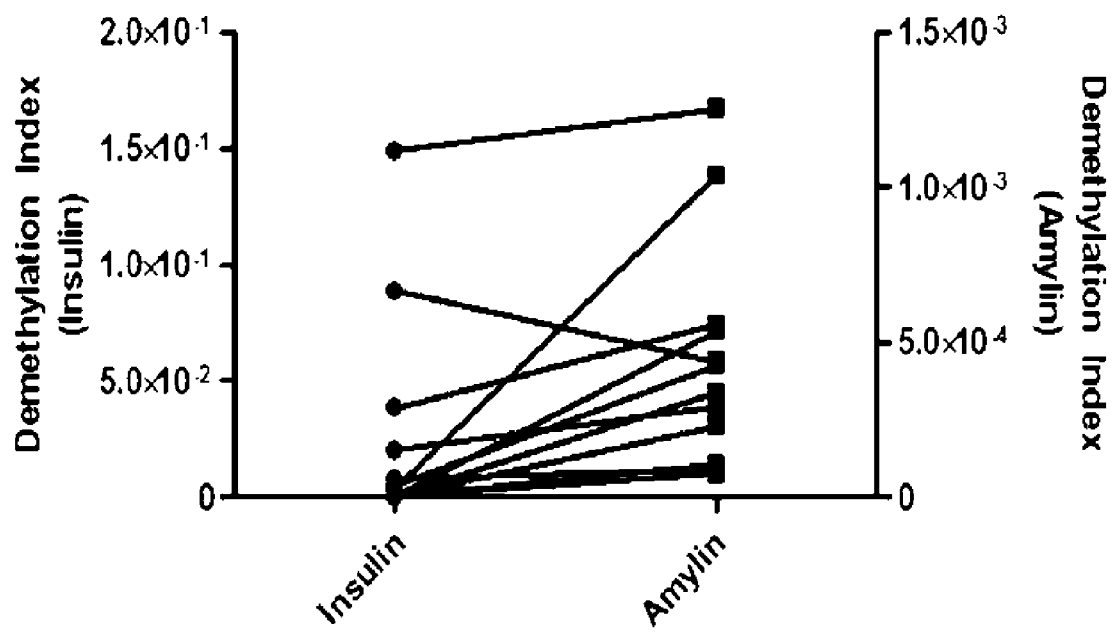
Figure 6A:
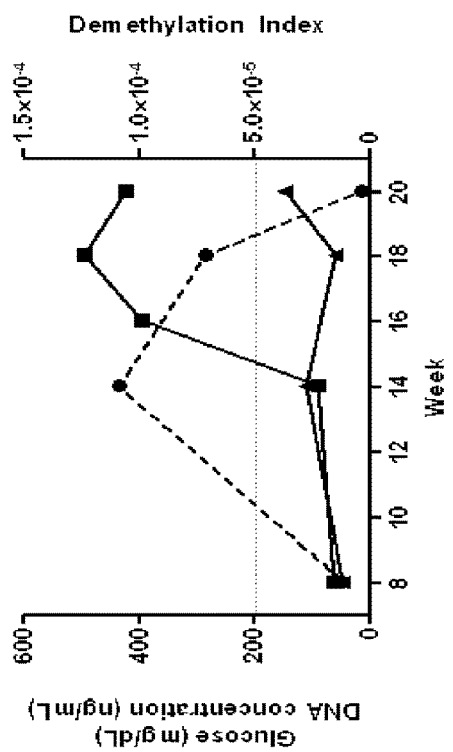
FIGS. 6A-6D show that demethylated amylin DNA is increased in the blood of pre-diabetic NOD mice during T1D progression. 8 wk old female NOD mice were housed in SPF conditions and monitored for 12 weeks for the development of diabetes. Blood from each animal was collected on wk 8, 14, 18 and 20. Representative data from four individual NOD mice are shown (FIGS. 6A, 6B, 6C, and 6D, respectively). DNA concentration in the serum was measured using picogreen. DMI was calculated on bisulfite treated serum-derived DNA. Variability in disease onset and β-cell DNA is characteristic of the spontaneous nature of T1D in the NOD mouse model.
Figure 6B:
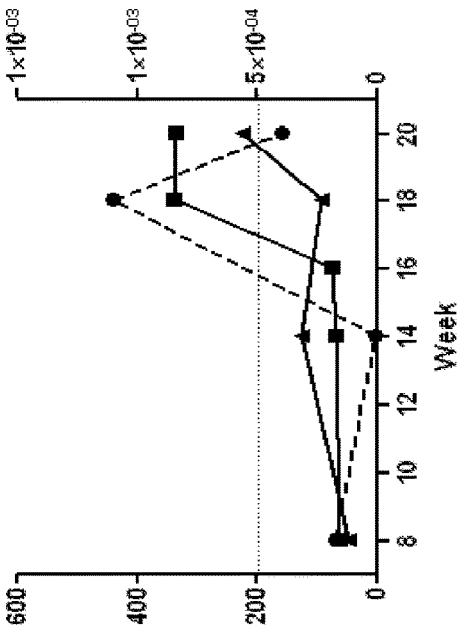
Figure 6C:
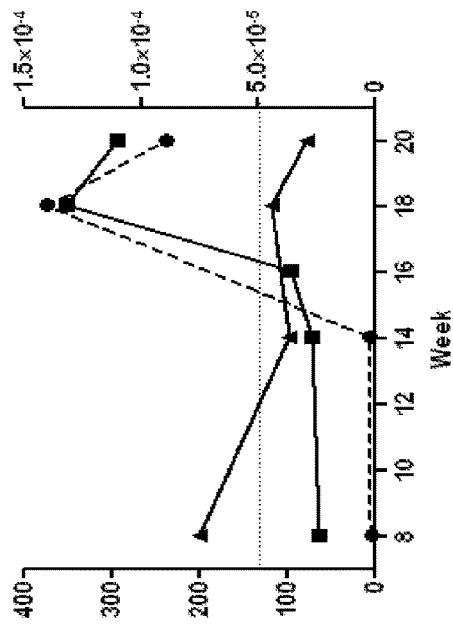
Figure 6D:
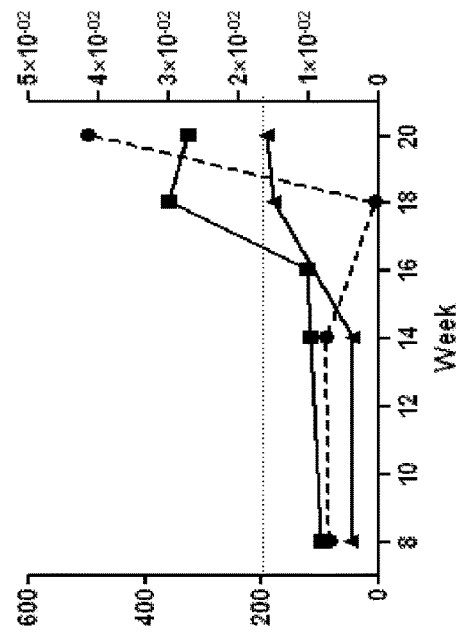

The ability of methylation-specific primers to detect β-cell derived amylin DNA in the blood of patients with recent onset (RO) T1D was therefore investigated. To this end, serum samples from RO T1D patients and age matched unrelated healthy controls (HC) from the Medical College of Wisconsin were processed and cfDNA extracted. qRTPCR of $1^{St}$ step products revealed a statistically significant increase in DeMeth DNA in the RO T1D group (FIG. 5A, p<0.015) when compared with HC individuals. ROC analysis showed an AUC of 0.866 with 95% confidence interval of 0.72-1.01. These analysis reached statistical significance (FIG. 5B, p<0.0017). Correlation analysis between DMI values and HbA1c at the time of sampling showed a modest positive correlation between impaired glycemic control and DMI values (FIG. 5C, R=0.458, p<0.083). Insulin DMI has been shown to be a useful biomarker of β-cell death in T1D. DMI levels of insulin were examined in the same patient cohort. Analysis of amylin and insulin signals showed that the increased levels of amylin DMI were associated with increased insulin DMI values (FIG. 5D, Pearson's r=0.63, p<0.028).

Primers specific for DeMeth Amylin detect an increase in β-cell DNA during diabetes progression in non-obese diabetic (NOD) mice. The NOD mouse model of human T1D is characterized by a loss of β-cells due to an aberrant autoimmune attack. DeMeth insulin DNA levels are increased during the natural progression of T1D in the NOD mouse, demonstrating the utility of DeMeth insulin DNA as a biomarker of β-cell loss during the period of prediabetes. DeMeth amylin DNA can be used for detecting β-cell loss in prediabetic NOD mice during disease progression and following T1D presentation. Cheek pouch bleeding was performed to collect cfDNA for analysis, thereby providing a unique opportunity to track the changes in β-cell death in the same animal. DMI values and glucose levels which were analyzed over a period of 12 weeks showed an increase in β-cell death during diabetes progression (FIG. 3A), which was previously shown to correlate with reduced insulin content in the pancreas and enhanced islet infiltration. Sample analyses of four individual NOD mice revealed a relatively stable level of total circulating DNA throughout the experiment, with DMI levels increased prior to or during the presentation of hyperglycemia (FIGS. 3D-3G). Taken together, these results demonstrate the ability of methylation-specific primers to detect an increase in circulating free amylin DNA during the progression of β-cell destruction in the NOD model of T1D.

TABLE 2

Patient demographics and clinical information

| Parameter | Groups Ctrl | T1D |
|---|---|---|
| N | 11 | 15 |
| Age | 13.13 ± 1.00 | 13.22 ± 066 |
| F/(M) | 5/(6) | 8/(7) |
| Age at Dx | — | 12.90 ± 0.68 |
| HbA1c | — | 7.5 ± 0.28% |
| # AutoAb | 0 | 3.18 ± 0.26 |

TABLE 3

Primer sequences and PCR protocols for mouse amylin analysis

| PCR Type | Primer Designation | Primer Sequence 5'→3' | Product Length | PCR Protocol |
|---|---|---|---|---|
| First-step PCR | Forward | TGGTAGTAATTTTT AGATGGATAAA SEQ ID NO: 001 | 178 bp | 50 Cycles, annealing temperature 57° C. |
| | Reverse | AAATTCCCTATTTA AATCCCCTAC SEQ ID NO: 002 | | |
| Methylation-specific nested qRTPCR | Hypermeth-specific forward | AAACGGAAGTGTAA TACGGTTAC SEQ ID NO: 003 | 122 bp | 40 Cycles, annealing temperature 63° C. |
| | Hypermeth-specific reverse | TTACCATATATATT CGATCCCACG SEQ ID NO: 004 | | |
| | Hypometh-specific forward | AAATGGAAGTGTAA TATGGTTAT SEQ ID NO: 005 | | |
| | Hypometh-specific reverse | TTACCATATATATT CAATCCCACA SEQ ID NO: 006 | | |

TABLE 4

Primer sequences and PCR protocols for human amylin analysis

| PCR Type | Primer Designation | Primer Sequence 5'→3' | Product Length | PCR Protocol |
|---|---|---|---|---|
| First-step PCR | Forward | TGTTATTAGTTATT AGGTGGAAAAG SEQ ID NO: 007 | 146 bp | 50 Cycles, annealing temperature 57° C. |
| | Reverse | TCTTACCATATATA TTAAATCCCAC SEQ ID NO: 008 | | |
| Methylation-specific nested qRTPCR | Common forward | TGTTATTAGTTATT AGGTGGAAAAG SEQ ID NO: 009 | 76 bp | 40 Cycles, annealing temperature 63° C. |
| | Hypermeth-specific reverse | TAAAAAATTTACCA AACGCTACG SEQ ID NO: 010 | | |
| | Hypometh-specific reverse | TAAAAAATTTACCA AACACTACA SEQ ID NO: 011 | | |
| Native Amylin PCR | Forward | TGTTACCAGTCATC AGGTGGAAAAG SEQ ID NO: 012 | 146 bp | 27-33 Cycles, annealing temperature 57° C. |
| | Reverse | TCTTGCCATATGTA TTGGATCCCAC SEQ ID NO: 013 | | |

TABLE 5

Sequences and protocols for human insulin analysis (See Akirav US 20150376706).

Methylation independent amplification of insulin DNA:
Forward primer:
SEQ ID NO: 014
GTGCGGTTTATATTTGGTGGAAGTT Reverse primer:
SEQ ID NO: 015
ACAACAATAAACAATTAACTCACCCTACAA Methylated insulin DNA (i.e., DNA not derived from a.beta. cell)(alternates):
Probe 1:
SEQ ID NO: 016
ACCTCCCGACGAATCT Probe 2:
SEQ ID NO: 017
TACCTCTCGTCGAATCT Demethylated insulin DNA (i.e., DNA derived from a.beta. cell)(alternates):
Probe 3:
SEQ ID NO: 018
ACCTCCCAACAAATCT Probe 4:
SEQ ID NO: 019
TACCTCCCATCAAATCT Outer amplification PCR according to Akirav et al., (2011):
Forward primer:
SEQ ID NO: 020
TTAGGGGTTTTAAGGTAGGGTATTTGGT Reverse primer:
SEQ ID NO: 021
ACCAAAAACAACAATAAACAATTAACTCACCCTACAA

TABLE 5-continued

Sequences and protocols for human insulin analysis (See Akirav US 20150376706).

Inner amplification PCR according to Akirav et al., (2011):
Methylated forward primer:
SEQ ID NO: 022
GTGGATGCGTTTTTTGTTTTTGTTGGC Methylated reverse primer:
SEQ ID NO: 023
CACCCTACAAATCCTCTACCTCCCG Demethylated forward primer:
SEQ ID NO. 024
TTGTGGATGTGTTTTTTGTTTTTGTTGGT Demethylated reverse primer:
SEQ ID NO: 025
CACCCTACAAATCCTCTACCTCCCA

Example 2

Methylation-Specific Analysis

As an alternate to use of qRTPCR, DNA probes may also be used to quantify the relationship between the demethylated (hypomethylated) DNA from β-cells, and methylated (hypermethylated) DNA from non-β-cell origin, from various sources, such as circulating DNA (serum), or DNA in saliva or urine, for example.

DNA from serum samples is purified using the Qiagen QIAamp DNA Blood Kit following the manufacturer-recommended protocol. Synthetic unmethylated and methylated DNA is available from Millipore. Purified DNA is quantitated using a NanoDrop 2000 spectrophotometer. As per Example 1, DNA is subjected to bisulfite treatment and purified on a DNA binding column to remove excessive bisulfite reagent using the Zymo EZ DNA Methylation Kit, and then amplified using PCR. Bisulfite-treated DNA template was added to ZymoTaq™ Premix (see, www.zymoresearch.com/protein/enzymes/zymotaq-dna-polymerase) Using the forward and reverse primers, PCR is conducted, and the PCR products excised from a 3% agarose gel.

```
Common Forward
                         SEQ ID NO. 007
TGTTATTAGTTATTAGGTGGAAAAG Common Reverse
                         SEQ ID NO. 008
TCTTACCATATATATTAAATCCCAC
```

The PCR product (or amplicon) is then detected by methylation status specific probes as follows. Probes for the detection of hypermethylated amylin DNA and hypomethylated amylin DNA are as follows:

```
Hypermethylated specific probe (non-β-cell)
                         SEQ ID NO: 026
AAACGCTACGTTACACA.

Hypomethlyated specific probe (β-cell)
                         SEQ ID NO: 027
AAACACTACATTACACA.
```

The disclosures of each and every patent, patent application, and publication cited herein are each hereby expressly incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

REFERENCES

Akirav E, Kushner J A, Herold K C (2008) β-cell mass and type 1 diabetes: Going, going, gone? Diabetes 57:2883-2888.

Akirav E M, Lebastchi J, Galvan E M, Henegariu O, Akirav M, Ablamunits V, Lizardi P M, Herold K C: Detection of beta cell death in diabetes using differentially methylated circulating DNA. Proceedings of the National Academy of Sciences of the United States of America 2011; 108: 19018-19023

Akirav, E. M., C. M. Bergman, M. Hill, and N. H. Ruddle. 2009. Depletion of CD4(+)CD25(+) T cells exacerbates experimental autoimmune encephalomyelitis induced by mouse, but not rat, antigens. J Neurosci Res 87:3511-3519.

Alberti K G, Zimmet P Z: Definition, diagnosis and classification of diabetes mellitus and its complications. Part 1: diagnosis and classification of diabetes mellitus provisional report of a WHO consultation. Diabet Med 1998; 15:539-553

Banerjee M, Otonkoski T: A simple two-step protocol for the purification of human pancreatic beta cells. Diabetologia 2009; 52:621-625

Barres, Romain, and Juleen R. Zierath. "DNA methylation in metabolic disorders." The American journal of clinical nutrition 93.4 (2011): 897S-900S.

Bartke T, et al. (2010) Nucleosome-interacting proteins regulated by DNA and histone methylation. Cell 143:470-484.

Basadonna G, Montorsi F, Kakizaki K, Merrell R C (1988) Cyclosporin A and islet function. Am J Surg 156:191-193.

Bell, Christopher G., et al. "Genome-wide DNA methylation analysis for diabetic nephropathy in type 1 diabetes mellitus." BMC medical genomics 3.1 (2010): 33.

Berney T, et al. (2006) Detection of insulin mRNA in the peripheral blood after human islet transplantion predicts deterioration of metabolic control. Am J Transplant 6:1704-1711.

Best C H, Haist R E, Ridout J H (1939) Diet and the insulin content of pancreas. J Physiol 97:107-119.

Bluestone J A, Herold K, Eisenbarth G (2010) Genetics, pathogenesis and clinical interventions in type 1 diabetes. Nature 464:1293-1300.

Boissy, A. R., and P. J. Ford. 2012. A touch of MS: therapeutic mislabeling. Neurology 78:1981-1985.

Bonifacio E, Scirpoli M, Kredel K, Fuchtenbusch M, Ziegler A G: Early autoantibody responses in prediabetes are IgG1 dominated and suggest antigen-specific regulation. Journal of immunology 1999; 163:525-532

Botezatu, Irina, Ol'ga Serdyuk, Galina Potapova, Valery Shelepov, Raisa Alechina, Yuriy Molyaka, Vitaliy Anan'ev, Igor Bazin, August Garin, Mehti Narimanov, Vasiliy Knysh, Hovsep Melkonyan, Samuil Umansky, and Anatoly Lichtenstein (2000) "Genetic Analysis of DNA Excreted in Urine: A New Approach for Detecting Specific Genomic DNA Sequences from Cells Dying in an Organism", Clinical Chemistry 46:8 1078-1084.

Bougneres P F, et al. (1988) Factors associated with early remission of type I diabetes in children treated with cyclosporine. N Engl J Med 318:663-670.

Bretherton-Watt D, Gore N, Boam D S: Insulin upstream factor 1 and a novel ubiquitous factor bind to the human islet amyloid polypeptide/amylin gene promoter. The Biochemical journal 1996; 313 (Pt 2):495-502

Bruck, W., C. Lucchinetti, and H. Lassmann. 2002. The pathology of primary progressive multiple sclerosis. Mult Scler 8:93-97. Polman, C. H., S. C. Reingold, B. Banwell, M. Clanet, J. A. Cohen, M. Filippi, K. Fujihara, E. Havrdova, M. Hutchinson, L. Kappos, F. D. Lublin, X. Montalban, P. O'Connor, M. Sandberg-Wollheim, A. J. Thompson, E. Waubant, B. Weinshenker, and J. S. Wolinsky. 2011. Diagnostic criteria for multiple sclerosis: 2010 revisions to the McDonald criteria. Ann Neurol 69:292-302.

Cauchi et al., Post genome-wide association studies of novel genes associated with type 2 diabetes show gene-gene interaction and high predictive value, PLoS One, 3(5): e2031 (2008).

Chen X Q, Stroun M, Magnenat J L, Nicod L P, Kurt A M, Lyautey J, Lederrey C, Anker P: Microsatellite alterations in plasma DNA of small cell lung cancer patients. Nature medicine 1996; 2:1033-1035

Collins T J (2007) ImageJ for microscopy. Biotechniques 43(Suppl 1):25-30.

Crowley E, Di Nicolantonio F, Loupakis F, Bardelli A: Liquid biopsy: monitoring cancer-genetics in the blood. Nature reviews Clinical oncology 2013; 10:472-484

Dayeh, Tasnim A., et al. "Identification of CpG-SNPs associated with type 2 diabetes and differential DNA methylation in human pancreatic islets." Diabetologia 56.5 (2013): 1036-1046.

Erlich H, et al.; Type 1 Diabetes Genetics Consortium (2008) HLA DR-DQ haplotypes and genotypes and type 1 diabetes risk: Analysis of the Type 1 Diabetes Genetics Consortium families Diabetes 57:1084-1092.

Eyre, Stephen, et al. "Overlapping genetic susceptibility variants between three autoimmune disorders: rheumatoid arthritis, type 1 diabetes and coeliac disease." Arthritis research & therapy 12.5 (2010): R175.

Fineman M, Weyer C, Maggs D G, Strobel S, Kolterman O G: The human amylin analog, pramlintide, reduces postprandial hyperglucagonemia in patients with type 2 diabetes mellitus. Hormone and metabolic research=Hormon- and Stoffwechselforschung=Hormones et metabolisme 2002; 34:504-508

Fradin, Delphine, et al. "Association of the CpG methylation pattern of the proximal insulin gene promoter with type 1 diabetes." PLoS One 7.5 (2012): e36278.

Fujiki, Katsunori, et al. "Expression of the peroxisome proliferator activated receptor γ gene is repressed by DNA methylation in visceral adipose tissue of mouse models of diabetes." BMC biology 7.1 (2009): 38.

Fujimoto K, et al. (2010) Loss of Nix in Pdx 1-deficient mice prevents apoptotic and necrotic 13 cell death and diabetes. J Clin Invest 120:4031-4039.

German M S, Moss L G, Wang J, Rutter W J: The insulin and islet amyloid polypeptide genes contain similar cell-specific promoter elements that bind identical beta-cell nuclear complexes. Molecular and cellular biology 1992; 12:1777-1788

Giddings S J, King C D, Harman K W, Flood J F, Carnaghi L R (1994) Allele-specific inactivation of insulin 1 and 2 in the mouse yolk sac indicates imprinting. Nat Genet 6:310-313.

Goldenberg, M. M. 2012. Multiple sclerosis review. P T 37:175-184.

Grady W M, Rajput A, Lutterbaugh J D, Markowitz S D (2001) Detection of aberrantly methylated hMLH1 promoter DNA in the serum of patients with microsatellite un-stable colon cancer. Cancer Res 61:900-902.

Greenbaum C J, et al.; Type 1 Diabetes Trial Net Research Group; European C-Peptide Trial Study Group (2008) Mixed-meal tolerance test versus glucagon stimulation test for the assessment of β-cell function in therapeutic trials in type 1 diabetes. Diabetes Care 31:1966-1971.

Hagopian W A, et al. (1995) Glutamate decarboxylase, insulin, and islet cell antibodies and HLA typing to detect diabetes in a general population-based study of Swedish children. J Clin Invest 95:1505-1511.

Hakonarson, Hakon, et al. "A genome-wide association study identifies KIAA0350 as a type 1 diabetes gene." Nature 448.7153 (2007): 591-594.

Herman J G, Graff J R, Myohanen S, Nelkin B D, Baylin S B: Methylation-specific PCR: a novel PCR assay for methylation status of CpG islands. Proceedings of the National Academy of Sciences of the United States of America 1996; 93:9821-9826

Hollander P A, Levy P, Fineman M S, Maggs D G, Shen L Z, Strobel S A, Weyer C, Kolterman O G: Pramlintide as an adjunct to insulin therapy improves long-term glycemic and weight control in patients with type 2 diabetes: a 1-year randomized controlled trial. Diabetes care 2003; 26:784-790

Husseiny M I, Kuroda A, Kaye A N, Nair I, Kandeel F, Ferreri K: Development of a quantitative methylation-specific polymerase chain reaction method for monitoring beta cell death in type 1 diabetes. PLoS one 2012; 7:e47942

Imagawa, Akihisa, et al. "A novel subtype of type 1 diabetes mellitus characterized by a rapid onset and an absence of diabetes-related antibodies." New England journal of medicine 342.5 (2000): 301-307.

Jayaraman S (2011) Assessment of beta cell viability. Curr Protoc Cytom 55:6.27.1-6.27.16.

Jones P A: Functions of DNA methylation: islands, start sites, gene bodies and beyond. Nature reviews Genetics 2012; 13:484-492

Kahn S E, D'Alessio D A, Schwartz M W, Fujimoto W Y, Ensinck J W, Taborsky G J, Jr., Porte D, Jr.: Evidence of cosecretion of islet amyloid polypeptide and insulin by beta-cells. Diabetes 1990; 39:634-638

Keymeulen B, et al. (2005) Insulin needs after CD3-antibody therapy in new-onset type 1 diabetes. N Engl J Med 352:2598-2608.

Kim, Myungjin, et al. "DNA methylation as a biomarker for cardiovascular disease risk." PloS one 5.3 (2010): e9692.

Klose R J, Bird A P (2006) Genomic DNA methylation: The mark and its mediators. Trends Biochem Sci 31:89-97.

Kuroda A, et al. (2009) Insulin gene expression is regulated by DNA methylation. PLoS ONE 4:e6953.

Kuroda A, Rauch T A, Todorov I, Ku H T, Al-Abdullah I H, Kandeel F, Mullen Y, Pfeifer G P, Ferreri K: Insulin gene expression is regulated by DNA methylation. PloS one 2009; 4:e6953

Lebastchi J, Deng S, Lebastchi A H, Beshar I, Gitelman S, Willi S, Gottlieb P, Akirav E M, Bluestone J A, Herold K C: Immune therapy and beta-cell death in type 1 diabetes. Diabetes 2013; 62:1676-1680

Leiter E H, et al. (2007) Unexpected functional consequences of xenogeneic transgene expression in β-cells of NOD mice. Diabetes Obes Metab 9(Suppl 2):14-22.

Lichtenstein, A. V., et al. (2001), "Circulating nucleic acids and apoptosis"; Ann NY Acad Sci, 945:239-249.

Lowe, Christopher E., et al. "Large-scale genetic fine mapping and genotype-phenotype associations implicate polymorphism in the IL2RA region in type 1 diabetes." Nature genetics 39.9 (2007): 1074-1082.

Ludvigsson J, Heding L (1982) Abnormal proinsulin/C-peptide ratio in juvenile diabetes. Acta Diabetol Lat 19:351-358.

Ludvik B, Thomaseth K, Nolan J J, Clodi M, Prager R, Pacini G: Inverse relation between amylin and glucagon secretion in healthy and diabetic human subjects. European journal of clinical investigation 2003; 33:316-322

Lukinius A, Wilander E, Westermark G T, Engstrom U, Westermark P: Co-localization of islet amyloid polypeptide and insulin in the B cell secretory granules of the human pancreatic islets. Diabetologia 1989; 32:240-244

Mackay, Deborah J G, et al. "Hypomethylation of multiple imprinted loci in individuals with transient neonatal diabetes is associated with mutations in ZFP57." Nature genetics 40.8 (2008): 949-951.

Maier, Sabine, and Alexander Olek. "Diabetes: a candidate disease for efficient DNA methylation profiling." The Journal of nutrition 132.8 (2002): 2440S-2443S.

McClymont, Stephanie A., et al. "Plasticity of human regulatory T cells in healthy subjects and patients with type 1 diabetes." The Journal of Immunology 186.7 (2011): 3918-3926.

Medarova Z, Tsai S, Evgenov N, Santamaria P, Moore A (2008) In vivo imaging of a diabetogenic CD8+ T cell response during type 1 diabetes progression. Magn Reson Med 59:712-720.

Miranda T B, Jones P A (2007) DNA methylation: The nuts and bolts of repression. J Cell Physiol 213:384-390.

Mosselman S, Hoppener J W, de Wit L, Soeller W, Lips C J, Jansz H S: IAPP/amylin gene transcriptional control region: evidence for negative regulation. FEBS letters 1990; 271:33-36

Müller H M, et al. (2003) DNA methylation in serum of breast cancer patients: An independent prognostic marker. Cancer Res 63:7641-7645.

Nawroz H, Koch W, Anker P, Stroun M, Sidransky D: Microsatellite alterations in serum DNA of head and neck cancer patients. Nature medicine 1996; 2:1035-1037

O'Brien T D, Westermark P, Johnson K H: Islet amyloid polypeptide and insulin secretion from isolated perfused pancreas of fed, fasted, glucose-treated, and dexamethasone-treated rats. Diabetes 1991; 40:1701-1706

Poitout V, et al. (1995) Morphological and functional characterization of 13 TC-6 cells: An insulin-secreting cell line derived from transgenic mice. Diabetes 44:306-313.

Prineas, J. W., and J. D. Parratt. 2012. Oligodendrocytes and the early multiple sclerosis lesion. Ann Neurol 72:18-31.

Rakyan, Vardhman K., et al. "Identification of type 1 diabetes-associated DNA methylation variable positions that precede disease diagnosis." PLoS Genet 7.9 (2011): e1002300.

Rashid, W., and D. H. Miller. 2008. Recent advances in neuroimaging of multiple sclerosis. Semin Neurol 28:46-55.Ceccarelli, A., R. Bakshi, and M. Neema. 2012. MRI in multiple sclerosis: a review of the current literature. Curr Opin Neurol 25:402-409.

Reidelberger R D, Haver A C, Arnelo U, Smith D D, Schaffert C S, Permert J: Amylin receptor blockade stimulates food intake in rats. American journal of physiology Regulatory, integrative and comparative physiology 2004; 287:R568-574

Riediger T, Zuend D, Becskei C, Lutz T A: The anorectic hormone amylin contributes to feeding-related changes of neuronal activity in key structures of the gut-brain axis. American journal of physiology Regulatory, integrative and comparative physiology 2004; 286:R114-122

Robertson, Keith D. "DNA methylation and human disease." Nature Reviews Genetics 6.8 (2005): 597-610.

Rudick, R. A., and A. E. Miller. 2012. Multiple sclerosis or multiple possibilities: the continuing problem of misdiagnosis. Neurology 78:1904-1906.

Ryan G J, Jobe L J, Martin R: Pramlintide in the treatment of type 1 and type 2 diabetes mellitus. Clinical therapeutics 2005; 27:1500-1512

Sapienza, Carmen, et al. "DNA methylation profiling identifies epigenetic differences between diabetes patients with ESRD and diabetes patients without nephropathy." Epigenetics 6.1 (2011): 20-28.

Sapienza, Carmen, et al. "DNA methylation profiling identifies epigenetic differences between diabetes patients with ESRD and diabetes patients without nephropathy." Epigenetics 6.1 (2011): 20-28.

Sherr J, Sosenko J, Skyler J S, Herold K C (2008) Prevention of type 1 diabetes: The time has come. Nat Clin Pract Endocrinol Metab 4:334-343.

Sherry N A, et al. (2006) Effects of autoimmunity and immune therapy on β-cell turnover in type 1 diabetes. Diabetes 55:3238-3245.

Sladek, Robert, et al. "A genome-wide association study identifies novel risk loci for type 2 diabetes." Nature 445.7130 (2007): 881-885.

Snorgaard O, Lassen L H, Binder C (1992) Homogeneity in pattern of decline of β-cell function in IDDM: Prospective study of 204 consecutive cases followed for 7.4 yr. Diabetes Care 15:1009-1013.

Solomon, A. J., E. P. Klein, and D. Bourdette. 2012. "Undiagnosing" multiple sclerosis: the challenge of misdiagnosis in MS. Neurology 78:1986-1991.

Sosenko J M, et al.; Diabetes Prevention Trial Type 1 Study Group (2007) Increasing the accuracy of oral glucose tolerance testing and extending its application to individuals with normal glucose tolerance for the prediction of type 1 diabetes: The Diabetes Prevention Trial Type 1. Diabetes Care 30:38-42.

Spelios M G, Kenna L A, Wall B, Akirav E M: In vitro formation of beta cell pseudoislets using islet-derived endothelial cells. PloS one 2013; 8:e72260

Steele C, et al. (2004) Insulin secretion in type 1 diabetes. Diabetes 53:426-433.

Stefan, Mihaela, et al. "DNA methylation profiles in type 1 diabetes twins point to strong epigenetic effects on etiology." Journal of autoimmunity 50 (2014): 33-37.

Suschek, C., K. Fehsel, K. D. Kroncke, A. Sommer, and V. Kolb-Bachofen. 1994. Primary cultures of rat islet capillary endothelial cells. Constitutive and cytokine-inducible macrophagelike nitric oxide synthases are expressed and activities regulated by glucose concentration. Am J Pathol 145:685-695.

Tenidis K, Waldner M, Bernhagen J, Fischle W, Bergmann M, Weber M, Merkle M L, Voelter W, Brunner H, Kapurniotu A: Identification of a penta- and hexapeptide of islet amyloid polypeptide (IAPP) with amyloidogenic and cytotoxic properties. Journal of molecular biology 2000; 295:1055-1071

Todd, John A. "Etiology of type 1 diabetes." Immunity 32.4 (2010): 457-467.

Toperoff, Gidon, et al. "Genome-wide survey reveals predisposing diabetes type 2-related DNA methylation variations in human peripheral blood." Human molecular genetics 21.2 (2012): 371-383.

Trudeau J D, et al. (2000) Neonatal β-cell apoptosis: A trigger for autoimmune diabetesβ Diabetes 49:1-7.

Umansky, S. R., et al. (1982) "In vivo DNA degradation of thymocytes of gamma-irradiated or hydrocortisone-treated rats"; Biochim Biophys. Acta 655:9-17.

Verge C F, et al. (1996) Prediction of type I diabetes in first-degree relatives using a combination of insulin, GAD, and ICA512bdc/IA-2 autoantibodies. Diabetes 45:926-933.

Volkmar, Michael, et al. "DNA methylation profiling identifies epigenetic dysregulation in pancreatic islets from type 2 diabetic patients." The EMBO journal 31.6 (2012): 1405-1426.

Waldron-Lynch F, Herold K C (2009) Advances in type 1 diabetes therapeutics: Immunomodulation and β-cell salvage. Endocrinol Metab Clin North Am 38:303-317.

Wallace, Chris, et al. "The imprinted DLK1-MEG3 gene region on chromosome 14q32. 2 alters susceptibility to type 1 diabetes." Nature genetics 42.1 (2010): 68-71.

Wallner M, et al. (2006) Methylation of serum DNA is an independent prognostic marker in colorectal cancer. Clin Cancer Res 12:7347-7352.

Wang G G, Allis C D, Chi P (2007) Chromatin remodeling and cancer, part II: ATP-dependent chromatin remodeling. Trends Mol Med 13:373-380.

Wang, Zhen, et al. "DNA methylation impairs TLR9 induced Foxp3 expression by attenuating IRF-7 binding activity in fulminant type 1 diabetes." Journal of autoimmunity 41 (2013): 50-59.

Wegner, C., M. M. Esiri, S. A. Chance, J. Palace, and P. M. Matthews. 2006. Neocortical neuronal, synaptic, and glial loss in multiple sclerosis. Neurology 67:960-967.

Westermark P, Andersson A, Westermark G T: Islet amyloid polypeptide, islet amyloid, and diabetes mellitus. Physiological reviews 2011; 91:795-826

Westermark P, Wernstedt C, Wilander E, Hayden D W, O'Brien T D, Johnson K H: Amyloid fibrils in human insulinoma and islets of Langerhans of the diabetic cat are derived from a neuropeptide-like protein also present in normal islet cells. PNAS 1987; 84:3881-3885

Whitehouse F, Kruger D F, Fineman M, Shen L, Ruggles J A, Maggs D G, Weyer C, Kolterman O G: A randomized study and open-label extension evaluating the long-term efficacy of pramlintide as an adjunct to insulin therapy in type 1 diabetes. Diabetes care 2002; 25:724-730

Yang, Beatrice T., et al. "Increased DNA methylation and decreased expression of PDX-1 in pancreatic islets from patients with type 2 diabetes." Molecular endocrinology 26.7 (2012): 1203-1212.

Yang, Beatrice T., et al. "Insulin promoter DNA methylation correlates negatively with insulin gene expression and positively with HbA1c levels in human pancreatic islets." Diabetologia 54.2 (2011): 360-367.

Zeggini, Eleftheria, et al. "Meta-analysis of genome-wide association data and large-scale replication identifies additional susceptibility loci for type 2 diabetes." Nature genetics 40.5 (2008): 638-645.

U.S. Pat. Nos. 6,492,144; 6,635,452; 6,835,541; 6,929,938; 6,943,240; 6,949,633; 6,989,245; 6,991,903; 7,037,652; 7,098,015; 7,132,519; 7,159,740; 7,192,736; 7,301,016; 7,332,275; 7,364,897; 7,419,787; 7,432,342; 7,435,541; 7,442,506; 7,449,297; 7,459,274; 7,510,835; 7,572,886; 7,608,394; 7,611,870; 7,618,936; 7,668,658; 7,696,316; 7,718,364; 7,727,720; 7,749,702; 7,759,065; 7,763,242; 7,781,161; 7,781,413; 7,785,843; 7,794,929; 7,803,529; 7,820,378; 7,829,283; 7,858,317; 7,867,714; 7,879,989; 7,951,563; 7,981,603; 8,034,792; 8,088,573; 8,088,581; 8,129,120; 8,150,626; 8,150,627; 8,163,279; 8,163,896; 8,206,926; 8,206,927; 8,207,316; 8,211,700; 8,229,677; 8,268,549; 8,314,068; 8,338,416; 8,361,731; 8,367,362; 8,367,806; 8,377,888; 8,404,640; 8,440,404; 8,445,211; 8,450,061; 8,455,221; 8,460,872; 8,467,976; 8,470,307; 8,476,013; 8,486,623; 8,497,066; 8,513,401; 8,568,984; 8,586,313; 8,598,135; 8,614,063; 8,652,780; 8,664,194; 8,673,571; 8,679,741; 8,680,069; 8,688,388; 8,691,507; 8,700,338; 8,703,425; 8,709,726; 8,710,200; 8,712,697; 8,715,926; 8,722,336; 8,728,815; 8,735,078; 8,754,062; 8,756,020; 8,758,995; 8,771,948; 8,784,772; 8,796,182; 8,818,735; 8,822,663; 8,841,256; 8,852,864; 8,859,502; 8,895,245; 8,900,565; 8,900,829; 8,927,209; 8,951,736; 8,962,236; 8,962,247; 8,969,313; 8,980,864; 8,992,910; 8,999,380; 9,034,580; 9,050,297; 9,061,059; 9,074,013; 9,086,403; 9,089,604; 9,090,944; 9,095,552; 9,107,886; 9,114,113; 9,127,312; 9,127,317; 9,141,756; 9,145,438; 9,149,506; 9,173,961; 9,175,331; 9,181,317; 9,181,319; 9,186,372; 9,187,780; 9,192,651; RE39,920; RE41,005; RE44,693; 20020006653; 20020009777; 20020037538; 20020039736; 20020098530; 20020115090; 20020119466; 20020119478; 20030017454; 20030068616; 20030069199; 20030087382; 20030092095; 20030104358; 20030104523; 20030138783; 20030180748; 20030186337; 20030224376; 20030232351; 20040002082; 20040005294; 20040006016; 20040022764; 20040023206; 20040023207; 20040033509; 20040048279; 20040058355; 20040081976; 20040137474; 20040219559; 20040234973; 20040234997; 20050003341; 20050020527; 20050026183; 20050064406; 20050112604; 20050164233; 20050164246; 20050191640; 20050202490; 20050221314; 20050255458; 20050260630; 20050266470; 20050266552; 20050272065; 20050288226; 20060003359; 20060009632; 20060051768; 20060088907; 20060121452; 20060121467; 20060160105; 20060204988; 20060211009; 20060211752; 20060246496; 20060257905; 20060286576; 20070015156; 20070037203; 20070042365; 20070042384; 20070048738; 20070087358; 20070141582; 20070161029; 20070178458; 20070178478; 20070196337; 20070202499; 20070231797; 20070238115; 20070264653; 20070281934; 20070292866; 20080064029; 20080076117; 20080081333; 20080096766; 20080108093; 20080113399; 20080118926; 20080138313; 20080175822; 20080213781; 20080213782; 20080242638; 20080249118; 20080254447; 20080254474; 20080260743; 20080261217; 20080299551; 20080299566; 20080305473; 20090005268; 20090047212; 20090047656; 20090047666; 20090068657; 20090075260; 20090093424; 20090105145; 20090111120; 20090130659; 20090136944; 20090142302; 20090155786; 20090155791; 20090162329; 20090162836; 20090186359; 20090186360; 20090191548; 20090215066; 20090220980; 20090232767; 20090252742; 20090253584; 20090263860; 20090264306; 20090270479; 20090280479; 20090298054; 20090298910; 20090305234; 20090305250; 20090317810; 20090326209; 20100004304; 20100021482; 20100035246; 20100047779; 20100062447; 20100068720; 20100124742; 20100129828; 20100129844; 20100130375; 20100130418; 20100135970; 20100136010; 20100136539; 20100136571; 20100136572; 20100143902; 20100143929; 20100151456; 20100151468; 20100167297; 20100172880; 20100184027; 20100191040; 20100196426; 20100227319; 20100233703; 20100233707; 20100234242; 20100261180; 20100297655; 20100303795; 20100304372; 20100311683; 20100317000; 20100330567; 20110003284; 20110003704; 20110003753; 20110003885; 20110014204; 20110028333; 20110039719; 20110053157; 20110053882; 20110076726; 20110091970; 20110097727; 20110104695; 20110104701; 20110117111; 20110158975; 20110159509; 20110160091; 20110160216; 20110165565; 20110165581; 20110171632; 20110171637; 20110190161; 20110195021; 20110207129; 20110212444; 20110229876; 20110244458; 20110256121; 20110262910; 20110269123; 20110269126; 20110294699; 20110301050; 20120009601; 20120015366; 20120028817; 20120053073; 20120071418; 20120094844; 20120094925; 20120100997; 20120108445; 20120129729; 20120142546; 20120148561; 20120178918; 20120184449;

| | | | | | |
|---|---|---|---|---|---|
| 20120184455; | 20120189540; | 20120196827; | WO1995010271; | WO1996033703; | WO1998039429; |
| 20120202202; | 20120208711; | 20120220475; | WO2000073509; | WO2001021836; | WO2001030972; |
| 20120238610; | 20120251499; | 20120264618; | WO2001055449; | WO2001062927; | WO2001071027; |
| 20120264640; | 20120276542; | 20120322072; | WO2001090304; | WO2002020754; | WO2002026936; |
| 20120329712; | 20130011380; | 20130011497; | WO2002055705; | WO2002079473; | WO2002097031; |
| 20130023430; | 20130034881; | 20130040906; | WO2003042357; | WO2003060069; | WO2003062376; |
| 20130065228; | 20130065836; | 20130071842; | WO2003066877; | WO2004016750; | WO2004023973; |
| 20130084286; | 20130084287; | 20130084328; | WO2004048555; | WO2004050858; | WO2004050860; |
| 20130085115; | 20130085681; | 20130102758; | WO2004050900; | WO2004053106; | WO2004081535; |
| 20130103320; | 20130116144; | 20130129668; | WO2004089301; | WO2004092338; | WO2005018669; |
| 20130130923; | 20130131194; | 20130137086; | WO2005027713; | WO2005040219; | WO2005081943; |
| 20130143969; | 20130150253; | 20130156727; | WO2005110474; | WO2005115452; | WO2005118641; |
| 20130156814; | 20130157879; | 20130164279; | WO2006063356; | WO2006066078; | WO2007001399; |
| 20130189684; | 20130224738; | 20130230850; | WO2007109857; | WO2007112330; | WO2007126876; |
| 20130230858; | 20130237445; | 20130261983; | WO2008002933; | WO2008019199; | WO2008025069; |
| 20130288241; | 20130288244; | 20130288918; | WO2008030539; | WO2008042407; | WO2008062105; |
| 20130296183; | 20130303555; | 20130304392; | WO2008105886; | WO2008109142; | WO2008127735; |
| 20130309666; | 20130309668; | 20130310260; | WO2008130516; | WO2008134729; | WO2009007852; |
| 20130310334; | 20130310406; | 20130315860; | WO2009032145; | WO2009032782; | WO2009092133; |
| 20130316931; | 20130324543; | 20130325360; | WO2009095436; | WO2009126304; | WO2009126380; |
| 20130338020; | 20130338933; | 20140031257; | WO2009131712; | WO2009155477; | WO2010018731; |
| 20140037576; | 20140038840; | 20140039154; | WO2010033658; | WO2010037001; | WO2010102267; |
| 20140045180; | 20140080715; | 20140093873; | WO2010108126; | WO2010141801; | WO2010144358; |
| 20140100792; | 20140113286; | 20140128283; | WO2011025852; | WO2011028531; | WO2011091048; |
| 20140137274; | 20140155279; | 20140178339; | WO2011097218; | WO2011113819; | WO2011126806; |
| 20140179805; | 20140180594; | 20140186827; | WO2011130402; | WO2011130624; | WO2011135088; |
| 20140187430; | 20140187537; | 20140194317; | WO2012019041; | WO2012024543; | WO2012033537; |
| 20140194319; | 20140194613; | 20140206014; | WO2012049211; | WO2012092379; | WO2012115885; |
| 20140206015; | 20140206639; | 20140222443; | WO2012120374; | WO2012162660; | WO2012164936; |
| 20140235474; | 20140242588; | 20140243218; | WO2012178007; | WO2013019623; | WO2013026015; |
| 20140249041; | 20140255418; | 20140271657; | WO2013052523; | WO2013055985; | WO2013067451; |
| 20140272967; | 20140272968; | 20140274753; | WO2013078372; | WO2013084002; | WO2013089819; |
| 20140274908; | 20140275281; | 20140302042; | WO2013090186; | WO2013090648; | WO2013119326; |
| 20140315203; | 20140322354; | 20140322719; | WO2013126813; | WO2013130161; | WO2013131083; |
| 20140328863; | 20140349291; | 20140363812; | WO2013132044; | WO2013151638; | WO2014008426; |
| 20140371188; | 20150004158; | 20150005176; | WO2014020124; | WO2014036314; | WO2014043763; |
| 20150011403; | 20150024952; | 20150025123; | WO2014066848; | WO2014093701; | WO2014093924; |
| 20150044288; | 20150051084; | 20150057183; | WO2014130770; | WO2014131845; | WO2014134084; |
| 20150065355; | 20150086543; | 20150086989; | WO2014138133; | WO2014144932; | WO2014152211; |
| 20150087529; | 20150099266; | 20150100244; | WO2014153063; | WO2014153111; | WO2014173814; |
| 20150104440; | 20150119350; | 20150126374; | WO2014189787; | WO2014191364; | WO2014193611; |
| 20150141275; | 20150141362; | 20150152505; | WO2014204726; | WO2014204728; | WO2014204729; |
| 20150167099; | 20150176079; | 20150191796; | WO2015006811; | WO2015018805; | WO2015038924; |
| 20150202261; | 20150203850; | 20150233933; | WO2015042708; | WO2015051173; | WO2015051302; |
| 20150275216; | 20150275298; | 20150284783; | WO2015051304; | WO2015078929; | WO2015089277; |
| 20150299119; | 20150299322; | 20150299810; | WO2015089419; | WO2015089465; | WO2015089486; |
| 20150307947; | 20150309026; | 20150322511; | WO2015089511; | WO2015138870; | WO2015159292; |
| 20150322512; | 20150322513; and PCT Nos. | | WO2015159293; | WO2015164228; | WO2015168587; |
| | | | WO2015168621; and WO2015184326. | | |

What is claimed is:

1. A method for monitoring β cell death, comprising:
extracting and purifying DNA from a body fluid of a human or animal;
treating the extracted purified DNA with bisulfite to convert demethylated cytosine to uracil while sparing the methylated cytosines;
amplifying the bisulfite-treated DNA using a polymerase chain reaction using primers for both demethylated amylin DNA of β cell origin and methylated amylin DNA of non-β cell origin;
performing a methylation sensitive detection to quantitatively distinguish between demethylated amylin DNA of β cell origin and methylated amylin DNA of non-β cell origin; and
computing a quantitative relationship between methylated amylin DNA and demethylated amylin DNA,
wherein the amplifying comprises conducting polymerase chain reaction using:

a forward primer:
SEQ ID NO: 007
TGTTATTAGTTATTAGGTGGAAAAG;
and a reverse primer
SEQ ID NO: 008
TCTTACCATATATATTAAATCCCAC.

2. The method according to claim 1, wherein the methylation sensitive detection comprises conducting quantitative real-time polymerase chain reaction using:
a common forward primer:

SEQ ID NO: 009
TGTTATTAGTTATTAGGTGGAAAAG;

a hypermethylated-DNA specific reverse primer:
SEQ ID NO: 010
TAAAAAATTTACCAAACGCTACG;
and a hypomethylated-DNA specific reverse primer:
SEQ ID NO: 011
TAAAAAATTTACCAAACACTACA.

3. The method according to claim 1, wherein the body fluid is derived from blood.

4. The method according to claim 1, wherein the body fluid is derived from saliva.

5. The method according to claim 1, wherein the body fluid is derived from urine.

6. The method according to claim 1, further comprising performing a polymerase chain reaction with methylation-status independent primers.

7. The method according to claim 6, wherein the performing a methylation sensitive detection comprises performing a further polymerase chain reaction with methylation-status dependent primers.

8. The method according to claim 1, wherein the performing the methylation sensitive detection comprises quantitatively determining a fluorescence associated with a DNA probe.

9. A method for monitoring cell death of islet β-cells, which release cellular DNA into body fluids upon cell death, comprising:
extracting and purifying DNA from a body fluid containing DNA from the islet β-cells; treating the extracted purified DNA with bisulfite to convert cytosine to uracil while sparing the CpG methylated cytosines;
amplifying a region of the bisulfite-treated DNA that comprises at least a portion of the amylin gene that is hypomethylated in insulin-producing cells and hypermethylated in non-insulin-producing cells, by polymerase chain reaction using DNA CpG methylation pattern independent primers, to thereby separately amplify converted hypomethylated amylin DNA and spared hyperemethylated amylin DNA;

detecting PCR products using a hypermethylated DNA-specific probe:
SEQ ID NO: 026
AAACGCTACGTTACACA,
and a hypomethylated DNA-specific probe:
SEQ ID NO: 027
AAACACTACATTACACA,
and
determining a quantitative relationship between converted hypomethylated amylin DNA and spared hyperemethylated amylin DNA.

10. The method according to claim 9, wherein the amplifying comprises conducting polymerase chain reaction using:

a forward primer:
SEQ ID NO: 007
TGTTATTAGTTATTAGGTGGAAAAG;
and a reverse primer
SEQ ID NO: 008
TCTTACCATATATATTAAATCCCAC.

11. The method according to claim 9, wherein the body fluid is derived from blood.

12. The method according to claim 9, wherein the body fluid is derived from saliva.

13. The method according to claim 9, wherein the body fluid is derived from urine.

14. The method according to claim 9, further comprising quantitatively determining at least an amount of demethylated insulin DNA.

15. The method according to claim 14, further comprising jointly processing the determined quantitative relationship between converted hypomethylated amylin DNA and spared hyperemethylated amylin DNA and the at least an amount of demethylated insulin DNA.

* * * * *